(12) United States Patent
Katz et al.

(10) Patent No.: US 8,852,902 B2
(45) Date of Patent: Oct. 7, 2014

(54) PRODUCING A TRIMETHYLPENTANOIC ACID USING HYBRID POLYKETIDE SYNTHASES

(75) Inventors: Leonard Katz, Oakland, CA (US); Jeffrey L. Fortman, San Francisco, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/302,966

(22) Filed: Nov. 22, 2011

(65) Prior Publication Data

US 2012/0219998 A1  Aug. 30, 2012

Related U.S. Application Data

(60) Provisional application No. 61/416,133, filed on Nov. 22, 2010.

(51) Int. Cl.
*C12N 15/52* (2006.01)
*C12P 7/40* (2006.01)

(52) U.S. Cl.
CPC .. *C12N 15/52* (2013.01); *C12P 7/40* (2013.01)
USPC .......................................... 435/139; 435/106

(58) Field of Classification Search
CPC ............... C12N 15/1068; C12N 15/52; C12N 15/1065; C12N 15/1089; C12N 9/22; C12N 15/113; C12N 15/85; C12N 5/0617; C12N 9/99
USPC .......................................................... 435/139
See application file for complete search history.

(56) References Cited

U.S. PATENT DOCUMENTS

| | | | |
|---|---|---|---|
| 3,839,378 A | 10/1974 | Yamaguchi et al. | |
| 5,234,719 A | 8/1993 | Richter et al. | |
| 5,672,491 A | 9/1997 | Khosla et al. | |
| 5,712,146 A | 1/1998 | Khosla et al. | |
| 5,830,750 A | 11/1998 | Khosla et al. | |
| 5,843,718 A | 12/1998 | Khosla et al. | |
| 6,262,340 B1 | 7/2001 | Betlach et al. | |
| 6,303,342 B1 | 10/2001 | Julien et al. | |
| 6,639,089 B2 | 10/2003 | Ito et al. | |
| 6,939,845 B2 | 9/2005 | Gautschi et al. | |
| 7,198,922 B2 | 4/2007 | Leadlay et al. | |
| 8,420,833 B2 * | 4/2013 | Katz et al. ............... | 549/273 |
| 2002/0045220 A1 | 4/2002 | Khosla et al. | |
| 2002/0192767 A1 | 12/2002 | Khosla et al. | |

FOREIGN PATENT DOCUMENTS

| | | |
|---|---|---|
| WO | WO 97/02358 A1 | 1/1997 |
| WO | WO 98/49315 A2 | 11/1998 |
| WO | WO 00/47724 A2 | 8/2000 |
| WO | WO 01/27306 A2 | 4/2001 |
| WO | WO 01/31035 A2 | 5/2001 |
| WO | WO 02/068613 A1 | 9/2002 |
| WO | WO 2006/024502 A2 | 3/2006 |
| WO | WO 2007/129770 A2 | 11/2007 |
| WO | WO 2009/121066 A2 | 10/2009 |

OTHER PUBLICATIONS

Hopwood. Genetic contributions to understanding PKS. Chemical Reviews. 97: 2465-2497. 1997.*
Anonymous: "Fatty acids," wayback, Mar. 15, 2008, retrieved from the internet: http://web.archive.org/web/20080315163005/http://www.cyberlipid.org/fa/acid0001.htm.
Ballini, R., et al., "A new synthesis of (±)-phoracantholide, (±)-dihydrorecifeiolide, and (±)- muscone via α-nitro ketones," *Liebigs Annalen*, vol. 1995(7), pp. 1381-1383 (Jul. 1, 1995).
Bisang et al.; "A chain initiation factor common to both modular and aromatic polyketide synthases," *Nature*, vol. 401, pp. 502-505 (1999).
Bush, K., et al., "Izumenolide—a novel β-lactamase inhibotor produced by Micromonospora. II. Biological properties," *The Jounal of Antiboitics*, vol. 33(11), pp. 1262-1269 (Nov. 1, 1980).
Clyne, D., et al., "They Synthesis of 14-Membered Macrocyclic Ethers," *Tetrahedron*, vol. 55(48), pp. 13659-13682 (Nov. 26, 1999).
Supplementary European Search Report from EP 09724907.2. (3 pages), Apr. 11, 2011.
Supplementary European Search Report from EP 09739701.2 (11 pages), Jun. 6, 2012.
Erb et al.; "Synthesis of C5-dicarboxylic acids from C2-units involving crotonyl-CoA carboxylase/reductase: the ethylnnalonyl-CoA pathway"; *Proc. Natl. Acad. Sci. U.S.A.*; 104(25):10631-10636 (Jun. 2007, Epub Jun. 4, 2007).
Hatcher, M., et al., "New silicon-mediated ring expansion of n-sized conjugated cycloalkenones into homoallylic n+3 lactones," *Tetrahedron Letters*, vol. 44(29), pp. 5407-5409 (Jul. 14, 2003).
Heathcote et al.; "Role of type II thioesterases: evidence for removal of short acyl chains produced by aberrant decarboxylation of chain extender units," *Chem Biol.*, vol. 8, No. 2, pp. 207-220 (2001).
Jacobsen et al.; "Precursor-Directed Biosynthesis of Erythromycin by Analogs by an Engineered Polyketide Synthase," *Science*, vol. 277, pp. 367-369 (1997).
Van Buijtenen, J., et al., "Switching from S-to R-selectivity in the *Candida antarctica* lipase B-catalyzed ring-opening of omega-methylated lactones: turning polymerizations by ring size," *Journal of the American Chemical Society*, vol. 129(23) (Jun. 1, 2007).

\* cited by examiner

*Primary Examiner* — Tekchand Saidha
*Assistant Examiner* — Rama P Ramanujam
(74) *Attorney, Agent, or Firm* — Kilpatrick Townsend & Stockton LLP

(57) ABSTRACT

The present invention provides for a polyketide synthase (PKS) capable of synthesizing trimethylpentanoic acid. The present invention also provides for a host cell comprising the PKS and when cultured produces the trimethylpentanoic acid. The present invention also provides for a method of producing the trimethylpentanoic acid, comprising: providing a host cell of the present invention, and culturing said host cell in a suitable culture medium such that the trimethylpentanoic acid is produced, optionally isolating the trimethylpentanoic acid, and optionally, reducing the isolated trimethylpentanoic acid into a trimethylpentanol or an iso-octane.

17 Claims, 8 Drawing Sheets

A

B

SEQUENCE LISTING

<160> NUMBER OF SEQ ID NOS: 13

<210> SEQ ID NO 1
<211> LENGTH: 309
<212> TYPE: PRT
<213> ORGANISM: Escherichia coli

<400> SEQUENCE: 1

Met Thr Thr Lys Lys Ala Asp Tyr Ile Trp Phe Asn Gly Glu Met Val

```
            1               5                  10                 15
        Arg Trp Glu Asp Ala Lys Val His Val Met Ser His Ala Leu His Tyr
                        20                  25                  30

Gly Thr Ser Val Phe Glu Gly Ile Arg Cys Tyr Asp Ser His Lys Gly
                    35                  40                  45

Pro Val Val Phe Arg His Arg Glu His Met Gln Arg Leu His Asp Ser
                50                  55                  60

Ala Lys Ile Tyr Arg Phe Pro Val Ser Gln Ser Ile Asp Glu Leu Met
        65                  70                  75                  80

Glu Ala Cys Arg Asp Val Ile Arg Lys Asn Asn Leu Thr Ser Ala Tyr
                        85                  90                  95

Ile Arg Pro Leu Ile Phe Val Gly Asp Val Gly Met Gly Val Asn Pro
                    100                 105                 110

Pro Ala Gly Tyr Ser Thr Asp Val Ile Ala Ala Phe Pro Trp Gly
                115                 120                 125

Ala Tyr Leu Gly Ala Glu Ala Leu Glu Gln Gly Ile Asp Ala Met Val
                    130                 135                 140

Ser Ser Trp Asn Arg Ala Ala Pro Asn Thr Ile Pro Thr Ala Ala Lys
        145                 150                 155                 160

Ala Gly Gly Asn Tyr Leu Ser Ser Leu Leu Val Gly Ser Glu Ala Arg
                        165                 170                 175

Arg His Gly Tyr Gln Glu Gly Ile Ala Leu Asp Val Asn Gly Tyr Ile
                    180                 185                 190

Ser Glu Gly Ala Gly Glu Asn Leu Phe Glu Val Lys Asp Gly Val Leu
                195                 200                 205

Phe Thr Pro Pro Phe Thr Ser Ser Ala Leu Pro Gly Ile Thr Arg Asp
                210                 215                 220

Ala Ile Ile Lys Leu Ala Lys Glu Leu Gly Ile Glu Val Arg Glu Gln
        225                 230                 235                 240

Val Leu Ser Arg Glu Ser Leu Tyr Leu Ala Asp Glu Val Phe Met Ser
                        245                 250                 255

Gly Thr Ala Ala Glu Ile Thr Pro Val Arg Ser Val Asp Gly Ile Gln
                    260                 265                 270

Val Gly Glu Gly Arg Cys Gly Pro Val Thr Lys Arg Ile Gln Gln Ala
                275                 280                 285

Phe Phe Gly Leu Phe Thr Gly Glu Thr Glu Asp Lys Trp Gly Trp Leu
                290                 295                 300

Asp Gln Val Asn Gln
        305

<210> SEQ ID NO 2
<211> LENGTH: 468
<212> TYPE: PRT
<213> ORGANISM: Bacillus subtilis

<400> SEQUENCE: 2

Met Val Val Gly Asp Phe Pro Ile Glu Thr Asp Thr Leu Val Ile Gly
        1               5                   10                  15

Ala Gly Pro Gly Gly Tyr Val Ala Ala Ile Arg Ala Ala Gln Leu Gly
                    20                  25                  30

Gln Lys Val Thr Val Val Glu Lys Ala Thr Leu Gly Gly Val Cys Leu
                35                  40                  45

Asn Val Gly Cys Ile Pro Ser Lys Ala Leu Ile Asn Ala Gly His Arg
        50                  55                  60
```

```
Tyr Glu Asn Ala Lys His Ser Asp Asp Met Gly Ile Thr Ala Glu Asn
 65                  70                  75                  80

Val Thr Val Asp Phe Thr Lys Val Gln Glu Trp Lys Ala Ser Val Val
                 85                  90                  95

Asn Lys Leu Thr Gly Gly Val Ala Gly Leu Leu Lys Gly Asn Lys Val
            100                 105                 110

Asp Val Val Lys Gly Glu Ala Tyr Phe Val Asp Ser Asn Ser Val Arg
        115                 120                 125

Val Met Asp Glu Asn Ser Ala Gln Thr Tyr Thr Phe Lys Asn Ala Ile
    130                 135                 140

Ile Ala Thr Gly Ser Arg Pro Ile Glu Leu Pro Asn Phe Lys Tyr Ser
145                 150                 155                 160

Glu Arg Val Leu Asn Ser Thr Gly Ala Leu Ala Leu Lys Glu Ile Pro
                165                 170                 175

Lys Lys Leu Val Val Ile Gly Gly Tyr Ile Gly Thr Glu Leu Gly
            180                 185                 190

Thr Ala Tyr Ala Asn Phe Gly Thr Glu Leu Val Ile Leu Glu Gly Gly
            195                 200                 205

Asp Glu Ile Leu Pro Gly Phe Glu Lys Gln Met Ser Ser Leu Val Thr
    210                 215                 220

Arg Arg Leu Lys Lys Lys Gly Asn Val Glu Ile His Thr Asn Ala Met
225                 230                 235                 240

Ala Lys Gly Val Glu Glu Arg Pro Asp Gly Val Thr Val Thr Phe Glu
                245                 250                 255

Val Lys Gly Glu Glu Lys Thr Val Asp Ala Asp Tyr Val Leu Ile Thr
            260                 265                 270

Val Gly Arg Arg Pro Asn Thr Asp Glu Leu Gly Leu Glu Gln Val Gly
        275                 280                 285

Ile Glu Met Thr Asp Arg Gly Ile Val Lys Thr Asp Lys Gln Cys Arg
    290                 295                 300

Thr Asn Val Pro Asn Ile Tyr Ala Ile Gly Asp Ile Ile Glu Gly Pro
305                 310                 315                 320

Pro Leu Ala His Lys Ala Ser Tyr Glu Gly Lys Ile Ala Ala Glu Ala
                325                 330                 335

Ile Ala Gly Glu Pro Ala Glu Ile Asp Tyr Leu Gly Ile Pro Ala Val
            340                 345                 350

Val Phe Ser Glu Pro Glu Leu Ala Ser Val Gly Tyr Thr Glu Ala Gln
        355                 360                 365

Ala Lys Glu Glu Gly Leu Asp Ile Val Ala Ala Lys Phe Pro Phe Ala
    370                 375                 380

Ala Asn Gly Arg Ala Leu Ser Leu Asn Glu Thr Asp Gly Phe Met Lys
385                 390                 395                 400

Leu Ile Thr Arg Lys Glu Asp Gly Leu Val Ile Gly Ala Gln Ile Ala
                405                 410                 415

Gly Ala Ser Ala Met Ile Ser Glu Leu Ser Leu Ala Ile Glu Gly Gly
            420                 425                 430

Met Thr Ala Glu Asp Ile Ala Met Thr Ile His Ala His Pro Thr Leu
        435                 440                 445

Gly Glu Ile Thr Met Glu Ala Ala Glu Val Ala Ile Gly Ser Pro Ile
    450                 455                 460

His Ile Val Lys
465
```

<210> SEQ ID NO 3
<211> LENGTH: 424
<212> TYPE: PRT
<213> ORGANISM: Bacillus subtilis

<400> SEQUENCE: 3

```
Met Ala Ile Glu Gln Met Thr Met Pro Gln Leu Gly Glu Ser Val Thr
 1               5                  10                  15

Glu Gly Thr Ile Ser Lys Trp Leu Val Ala Pro Gly Asp Lys Val Asn
             20                  25                  30

Lys Tyr Asp Pro Ile Ala Glu Val Met Thr Asp Lys Val Asn Ala Glu
         35                  40                  45

Val Pro Ser Ser Phe Thr Gly Thr Ile Thr Glu Leu Val Gly Glu Glu
     50                  55                  60

Gly Gln Thr Leu Gln Val Gly Glu Met Ile Cys Lys Ile Glu Thr Glu
 65                  70                  75                  80

Gly Ala Asn Pro Ala Glu Gln Lys Gln Glu Gln Pro Ala Ala Ser Glu
                 85                  90                  95

Ala Ala Glu Asn Pro Val Ala Lys Ser Ala Gly Ala Ala Asp Gln Pro
            100                 105                 110

Asn Lys Lys Arg Tyr Ser Pro Ala Val Leu Arg Leu Ala Gly Glu His
        115                 120                 125

Gly Ile Asp Leu Asp Gln Val Thr Gly Thr Gly Ala Gly Gly Arg Ile
130                 135                 140

Thr Arg Lys Asp Ile Gln Arg Leu Ile Glu Thr Gly Gly Val Gln Glu
145                 150                 155                 160

Gln Asn Pro Glu Glu Leu Lys Thr Ala Ala Pro Ala Pro Lys Ser Ala
                165                 170                 175

Ser Lys Pro Glu Pro Lys Glu Glu Thr Ser Tyr Pro Ala Ser Ala Ala
            180                 185                 190

Gly Asp Lys Glu Ile Pro Val Thr Gly Val Arg Lys Ala Ile Ala Ser
        195                 200                 205

Asn Met Lys Arg Ser Lys Thr Glu Ile Pro His Ala Trp Thr Met Met
210                 215                 220

Glu Val Asp Val Thr Asn Met Val Ala Tyr Arg Asn Ser Ile Lys Asp
225                 230                 235                 240

Ser Phe Lys Lys Thr Glu Gly Phe Asn Leu Thr Phe Ala Phe Phe
                245                 250                 255

Val Lys Ala Val Ala Gln Ala Leu Lys Glu Phe Pro Gln Met Asn Ser
            260                 265                 270

Met Trp Ala Gly Asp Lys Ile Ile Gln Lys Lys Asp Ile Asn Ile Ser
        275                 280                 285

Ile Ala Val Ala Thr Glu Asp Ser Leu Phe Val Pro Val Ile Lys Asn
290                 295                 300

Ala Asp Glu Lys Thr Ile Lys Gly Ile Ala Lys Asp Ile Thr Gly Leu
305                 310                 315                 320

Ala Lys Lys Val Arg Asp Gly Lys Leu Thr Ala Asp Asp Met Gln Gly
                325                 330                 335

Gly Thr Phe Thr Val Asn Asn Thr Gly Ser Phe Gly Ser Val Gln Ser
            340                 345                 350

Met Gly Ile Ile Asn Tyr Pro Gln Ala Ala Ile Leu Gln Val Glu Ser
        355                 360                 365

Ile Val Lys Arg Pro Val Val Met Asp Asn Gly Met Ile Ala Val Arg
370                 375                 380
```

```
Asp Met Val Asn Leu Cys Leu Ser Leu Asp His Arg Val Leu Asp Gly
385                 390                 395                 400

Leu Val Cys Gly Arg Phe Leu Gly Arg Val Lys Gln Ile Leu Glu Ser
            405                 410                 415

Ile Asp Glu Lys Thr Ser Val Tyr
            420

<210> SEQ ID NO 4
<211> LENGTH: 330
<212> TYPE: PRT
<213> ORGANISM: Bacillus subtilis

<400> SEQUENCE: 4

Met Ser Thr Asn Arg His Gln Ala Leu Gly Leu Thr Asp Gln Glu Ala
1               5                   10                  15

Val Asp Met Tyr Arg Thr Met Leu Leu Ala Arg Lys Ile Asp Glu Arg
                20                  25                  30

Met Trp Leu Leu Asn Arg Ser Gly Lys Ile Pro Phe Val Ile Ser Cys
            35                  40                  45

Gln Gly Gln Glu Ala Ala Gln Val Gly Ala Ala Phe Ala Leu Asp Arg
50                  55                  60

Glu Met Asp Tyr Val Leu Pro Tyr Tyr Arg Asp Met Gly Val Val Leu
65                  70                  75                  80

Ala Phe Gly Met Thr Ala Lys Asp Leu Met Met Ser Gly Phe Ala Lys
                85                  90                  95

Ala Ala Asp Pro Asn Ser Gly Gly Arg Gln Met Pro Gly His Phe Gly
            100                 105                 110

Gln Lys Lys Asn Arg Ile Val Thr Gly Ser Ser Pro Val Thr Thr Gln
        115                 120                 125

Val Pro His Ala Val Gly Ile Ala Leu Ala Gly Arg Met Glu Lys Lys
130                 135                 140

Asp Ile Ala Ala Phe Val Thr Phe Gly Glu Gly Ser Ser Asn Gln Gly
145                 150                 155                 160

Asp Phe His Glu Gly Ala Asn Phe Ala Ala Val His Lys Leu Pro Val
                165                 170                 175

Ile Phe Met Cys Glu Asn Asn Lys Tyr Ala Ile Ser Val Pro Tyr Asp
            180                 185                 190

Lys Gln Val Ala Cys Glu Asn Ile Ser Asp Arg Ala Ile Gly Tyr Gly
        195                 200                 205

Met Pro Gly Val Thr Val Asn Gly Asn Asp Pro Leu Glu Val Tyr Gln
210                 215                 220

Ala Val Lys Glu Ala Arg Glu Arg Ala Arg Arg Gly Glu Gly Pro Thr
225                 230                 235                 240

Leu Ile Glu Thr Ile Ser Tyr Arg Leu Thr Pro His Ser Ser Asp Asp
                245                 250                 255

Asp Asp Ser Ser Tyr Arg Gly Arg Glu Glu Val Glu Glu Ala Lys Lys
            260                 265                 270

Ser Asp Pro Leu Leu Thr Tyr Gln Ala Tyr Leu Lys Glu Thr Gly Leu
        275                 280                 285

Leu Ser Asp Glu Ile Glu Gln Thr Met Leu Asp Glu Ile Met Ala Ile
290                 295                 300

Val Asn Glu Ala Thr Asp Glu Ala Glu Asn Ala Pro Tyr Ala Ala Pro
305                 310                 315                 320

Glu Ser Ala Leu Asp Tyr Val Tyr Ala Lys
                325                 330
```

<210> SEQ ID NO 5
<211> LENGTH: 325
<212> TYPE: PRT
<213> ORGANISM: Bacillus subtilis

<400> SEQUENCE: 5

Met Ser Val Met Ser Tyr Ile Asp Ala Ile Asn Leu Ala Met Lys Glu
1               5                   10                  15

Glu Met Glu Arg Asp Ser Arg Val Phe Val Leu Gly Glu Asp Val Gly
            20                  25                  30

Arg Lys Gly Gly Val Phe Lys Ala Thr Ala Gly Leu Tyr Glu Gln Phe
        35                  40                  45

Gly Glu Glu Arg Val Met Asp Thr Pro Leu Ala Glu Ser Ala Ile Ala
50                  55                  60

Gly Val Gly Ile Gly Ala Ala Met Tyr Gly Met Arg Pro Ile Ala Glu
65                  70                  75                  80

Met Gln Phe Ala Asp Phe Ile Met Pro Ala Val Asn Gln Ile Ile Ser
                85                  90                  95

Glu Ala Ala Lys Ile Arg Tyr Arg Ser Asn Asn Asp Trp Ser Cys Pro
            100                 105                 110

Ile Val Val Arg Ala Pro Tyr Gly Gly Gly Val His Gly Ala Leu Tyr
        115                 120                 125

His Ser Gln Ser Val Glu Ala Ile Phe Ala Asn Gln Pro Gly Leu Lys
130                 135                 140

Ile Val Met Pro Ser Thr Pro Tyr Asp Ala Lys Gly Leu Leu Lys Ala
145                 150                 155                 160

Ala Val Arg Asp Glu Asp Pro Val Leu Phe Phe Glu His Lys Arg Ala
                165                 170                 175

Tyr Arg Leu Ile Lys Gly Glu Val Pro Ala Asp Asp Tyr Val Leu Pro
            180                 185                 190

Ile Gly Lys Ala Asp Val Lys Arg Glu Gly Asp Asp Ile Thr Val Ile
        195                 200                 205

Thr Tyr Gly Leu Cys Val His Phe Ala Leu Gln Ala Ala Glu Arg Leu
210                 215                 220

Glu Lys Asp Gly Ile Ser Ala His Val Val Asp Leu Arg Thr Val Tyr
225                 230                 235                 240

Pro Leu Asp Lys Glu Ala Ile Ile Glu Ala Ala Ser Lys Thr Gly Lys
                245                 250                 255

Val Leu Leu Val Thr Glu Asp Thr Lys Glu Gly Ser Ile Met Ser Glu
            260                 265                 270

Val Ala Ala Ile Ile Ser Glu His Cys Leu Phe Asp Leu Asp Ala Pro
        275                 280                 285

Ile Lys Arg Leu Ala Gly Pro Asp Ile Pro Met Ala Pro Thr Met
290                 295                 300

Glu Lys Tyr Phe Met Val Asn Pro Asp Lys Val Glu Ala Ala Met Arg
305                 310                 315                 320

Glu Leu Ala Glu Phe
                325

<210> SEQ ID NO 6
<211> LENGTH: 628
<212> TYPE: PRT
<213> ORGANISM: Salmonella typhimurium

<400> SEQUENCE: 6

-continued

```
Met Ser Phe Ser Glu Phe Tyr Gln Arg Ser Ile Asn Glu Pro Glu Ala
1               5                   10                  15

Phe Trp Ala Glu Gln Ala Arg Arg Ile Asp Trp Arg Gln Pro Phe Thr
            20                  25                  30

Gln Thr Leu Asp His Ser Arg Pro Pro Phe Ala Arg Trp Phe Cys Gly
        35                  40                  45

Gly Thr Thr Asn Leu Cys His Asn Ala Val Asp Arg Trp Arg Asp Lys
    50                  55                  60

Gln Pro Glu Ala Leu Ala Leu Ile Ala Val Ser Ser Glu Thr Asp Glu
65              70                  75                  80

Glu Arg Thr Phe Thr Phe Ser Gln Leu His Asp Glu Val Asn Ile Val
            85                  90                  95

Ala Ala Met Leu Leu Ser Leu Gly Val Gln Arg Gly Asp Arg Val Leu
            100                 105                 110

Val Tyr Met Pro Met Ile Ala Glu Ala Gln Ile Thr Leu Leu Ala Cys
        115                 120                 125

Ala Arg Ile Gly Ala Ile His Ser Val Val Phe Gly Gly Phe Ala Ser
    130                 135                 140

His Ser Val Ala Ala Arg Ile Asp Asp Ala Arg Pro Ala Leu Ile Val
145             150                 155                 160

Ser Ala Asp Ala Gly Ala Arg Gly Gly Lys Ile Leu Pro Tyr Lys Lys
            165                 170                 175

Leu Leu Asp Asp Ala Ile Ala Gln Ala Gln His Gln Pro Lys His Val
            180                 185                 190

Leu Leu Val Asp Arg Gly Leu Ala Lys Met Ala Trp Val Asp Gly Arg
        195                 200                 205

Asp Leu Asp Phe Ala Thr Leu Arg Gln Gln His Leu Gly Ala Ser Val
210                 215                 220

Pro Val Ala Trp Leu Glu Ser Asn Glu Thr Ser Cys Ile Leu Tyr Thr
225                 230                 235                 240

Ser Gly Thr Thr Gly Lys Pro Lys Gly Val Gln Arg Asp Val Gly Gly
            245                 250                 255

Tyr Ala Val Ala Leu Ala Thr Ser Met Asp Thr Ile Phe Gly Gly Lys
        260                 265                 270

Ala Gly Gly Val Phe Phe Cys Ala Ser Asp Ile Gly Trp Val Val Gly
    275                 280                 285

His Ser Tyr Ile Val Tyr Ala Pro Leu Leu Ala Gly Met Ala Thr Ile
290                 295                 300

Val Tyr Glu Gly Leu Pro Thr Tyr Pro Asp Cys Gly Val Trp Trp Lys
305                 310                 315                 320

Ile Val Glu Lys Tyr Gln Val Asn Arg Met Phe Ser Ala Pro Thr Ala
            325                 330                 335

Ile Arg Val Leu Lys Lys Phe Pro Thr Ala Gln Ile Arg Asn His Asp
        340                 345                 350

Leu Ser Ser Leu Glu Ala Leu Tyr Leu Ala Gly Glu Pro Leu Asp Glu
    355                 360                 365

Pro Thr Ala Ser Trp Val Thr Glu Thr Leu Gly Val Pro Val Ile Asp
370                 375                 380

Asn Tyr Trp Gln Thr Glu Ser Gly Trp Pro Ile Met Ala Leu Ala Arg
385                 390                 395                 400

Ala Leu Asp Asp Arg Pro Ser Arg Leu Gly Ser Pro Gly Val Pro Met
            405                 410                 415
```

-continued

```
Tyr Gly Tyr Asn Val Gln Leu Leu Asn Glu Val Thr Gly Glu Pro Cys
            420                 425                 430

Gly Ile Asn Glu Lys Gly Met Leu Val Ile Glu Gly Pro Leu Pro Pro
        435                 440                 445

Gly Cys Ile Gln Thr Ile Trp Gly Asp Asp Ala Arg Phe Val Lys Thr
    450                 455                 460

Tyr Trp Ser Leu Phe Asn Arg Gln Val Tyr Ala Thr Phe Asp Trp Gly
465                 470                 475                 480

Ile Arg Asp Ala Glu Gly Tyr Tyr Phe Ile Leu Gly Arg Thr Asp Asp
                485                 490                 495

Val Ile Asn Ile Ala Gly His Arg Leu Gly Thr Arg Glu Ile Glu Glu
            500                 505                 510

Ser Ile Ser Ser Tyr Pro Asn Val Ala Glu Val Ala Val Val Gly Ile
        515                 520                 525

Lys Asp Ala Leu Lys Gly Gln Val Ala Val Ala Phe Val Ile Pro Lys
    530                 535                 540

Gln Ser Asp Thr Leu Ala Asp Arg Glu Ala Ala Arg Asp Glu Glu Asn
545                 550                 555                 560

Ala Ile Met Ala Leu Val Asp Asn Gln Ile Gly His Phe Gly Arg Pro
                565                 570                 575

Ala His Val Trp Phe Val Ser Gln Leu Pro Lys Thr Arg Ser Gly Lys
            580                 585                 590

Met Leu Arg Arg Thr Ile Gln Ala Ile Cys Glu Gly Arg Asp Pro Gly
        595                 600                 605

Asp Leu Thr Thr Ile Asp Pro Ala Ser Leu Gln Gln Ile Arg Gln
    610                 615                 620

Ala Ile Glu Glu
625

<210> SEQ ID NO 7
<211> LENGTH: 646
<212> TYPE: PRT
<213> ORGANISM: Streptomyces coelicolor

<400> SEQUENCE: 7

Met Phe Asp Thr Val Leu Val Ala Asn Arg Gly Glu Ile Ala Val Arg
1               5                   10                  15

Val Ile Arg Thr Leu Arg Ser Met Gly Val Arg Ser Val Ala Val Phe
            20                  25                  30

Ser Asp Ala Asp Ala Asp Ala Arg His Val Arg Glu Ala Asp Asp Ala
        35                  40                  45

Val Arg Ile Gly Pro Ala Pro Ala Thr Glu Ser Tyr Leu Ser Val Glu
    50                  55                  60

Arg Leu Leu Ala Ala Ala Arg Thr Gly Ala Gln Ala Val His Pro
65                  70                  75                  80

Gly Tyr Gly Phe Leu Ala Glu Asn Ala Gly Phe Ala Arg Ala Cys Glu
                85                  90                  95

Glu Ala Gly Leu Val Phe Ile Gly Pro Ser Ala Asp Ala Ile Ala Leu
            100                 105                 110

Met Gly Asp Lys Ile Arg Ala Lys Glu Thr Val Arg Ala Ala Gly Val
        115                 120                 125

Pro Val Val Pro Gly Ser Ser Gly Ser Gly Leu Thr Asp Glu Gln Leu
    130                 135                 140

Ala Asp Ala Ala Arg Glu Ile Gly Thr Pro Val Leu Leu Lys Pro Ser
145                 150                 155                 160
```

```
Ala Gly Gly Gly Gly Lys Gly Met Arg Leu Val Arg Asp Thr Ala Val
            165                 170                 175

Leu Ala Asp Glu Ile Ala Ala Ala Arg Arg Glu Ala Arg Ala Ser Phe
        180                 185                 190

Gly Asp Asp Thr Leu Leu Val Glu Arg Trp Ile Asp Arg Pro Arg His
        195                 200                 205

Ile Glu Ile Gln Val Leu Ala Asp Gly His Gly Gly Val Val His Leu
        210                 215                 220

Gly Glu Arg Glu Cys Ser Leu Gln Arg Arg His Gln Lys Val Ile Glu
225                 230                 235                 240

Glu Ala Pro Ser Val Leu Leu Asp Glu Ala Thr Arg Ala Ala Met Gly
            245                 250                 255

Glu Ala Ala Val Gln Ala Ala Arg Ser Cys Gly Tyr Arg Gly Ala Gly
            260                 265                 270

Thr Val Glu Phe Ile Val Pro Gly Ser Asp Pro Ser Gln Tyr Tyr Phe
        275                 280                 285

Met Glu Met Asn Thr Arg Leu Gln Val Glu His Pro Val Thr Glu Leu
        290                 295                 300

Val Thr Gly Leu Asp Leu Val Glu Trp Gln Leu Arg Val Ala Ala Gly
305                 310                 315                 320

Glu Pro Leu Gly Phe Gly Gln Glu Asp Val Arg Leu Thr Gly His Ala
            325                 330                 335

Ile Glu Ala Arg Leu Cys Ala Glu Asp Pro Ala Arg Gly Phe Leu Pro
            340                 345                 350

Ser Gly Gly Thr Val Leu Arg Leu Arg Glu Pro Glu Gly Asp Gly Val
            355                 360                 365

Arg Thr Asp Ser Gly Leu Ser Glu Gly Thr Glu Val Gly Ser Leu Tyr
        370                 375                 380

Asp Pro Met Leu Ser Lys Val Ile Ala Tyr Gly Pro Asp Arg Glu Thr
385                 390                 395                 400

Ala Leu Arg Arg Leu Arg Ala Ala Leu Ala Gly Thr Val Thr Leu Gly
            405                 410                 415

Val Gln Thr Asn Ala Gly Phe Leu Arg Arg Leu Leu Ala His Pro Ala
            420                 425                 430

Val Val Ala Gly Glu Leu Asp Thr Gly Leu Val Glu Arg Glu Val Asp
            435                 440                 445

Gly Leu Val Ala Thr Asp Val Pro Glu Glu Val Tyr Glu Ala Ala Ala
        450                 455                 460

Ala Val Arg Leu Glu Ala Leu Arg Pro Arg Gly Asp Gly Trp Thr Asp
465                 470                 475                 480

Pro Phe Ser Val Pro Ser Gly Trp Arg Met Gly Gly Glu Pro Lys Ala
            485                 490                 495

Ala Ala Phe His Leu Arg Val Thr Asp Pro Val Glu His Thr Pro Arg
            500                 505                 510

Gly Thr His Thr Val Thr Gly Asp Arg Val Thr Val Thr Leu Asp Gly
            515                 520                 525

Val Arg His Thr Phe His Arg Ala Ala Asp Trp Leu Gly Arg Asp Gly
        530                 535                 540

Asp Ala Trp Gln Val Arg Asp His Asp Pro Val Ala Ala Ser Leu Asn
545                 550                 555                 560

Arg Ser Ala His Ala Gly Ala Asp Ser Leu Thr Ala Pro Met Pro Gly
            565                 570                 575
```

```
Thr Val Thr Val Val Lys Val Ala Val Gly Asp Glu Val Ser Ala Gly
            580                 585                 590

Gln Ser Leu Leu Val Val Glu Ala Met Lys Met Glu His Val Ile Ser
        595                 600                 605

Ala Pro His Ala Gly Thr Val Ala Glu Leu Asp Val Ala Pro Gly Thr
    610                 615                 620

Thr Val Ala Met Asp Gln Val Leu Ala Val Ile Ala Pro Thr Asp Asp
625                 630                 635                 640

Ala Thr Glu Glu Thr Ala
            645

<210> SEQ ID NO 8
<211> LENGTH: 530
<212> TYPE: PRT
<213> ORGANISM: Streptomyces coelicolor

<400> SEQUENCE: 8

Met Ser Glu Pro Glu Glu Gln Gln Pro Asp Ile His Thr Thr Ala Gly
1               5                   10                  15

Lys Leu Ala Asp Leu Arg Arg Ile Glu Glu Ala Thr His Ala Gly
            20                  25                  30

Ser Ala Arg Ala Val Glu Lys Gln His Ala Lys Gly Lys Leu Thr Ala
        35                  40                  45

Arg Glu Arg Ile Asp Leu Leu Leu Asp Glu Gly Ser Phe Val Glu Leu
50                  55                  60

Asp Glu Phe Ala Arg His Arg Ser Thr Asn Phe Gly Leu Asp Ala Asn
65                  70                  75                  80

Arg Pro Tyr Gly Asp Gly Val Val Thr Gly Tyr Gly Thr Val Asp Gly
            85                  90                  95

Arg Pro Val Ala Val Phe Ser Gln Asp Phe Thr Val Phe Gly Gly Ala
        100                 105                 110

Leu Gly Glu Val Tyr Gly Gln Lys Ile Val Lys Val Met Asp Phe Ala
    115                 120                 125

Leu Lys Thr Gly Cys Pro Val Val Gly Ile Asn Asp Ser Gly Gly Ala
130                 135                 140

Arg Ile Gln Glu Gly Val Ala Ser Leu Gly Ala Tyr Gly Glu Ile Phe
145                 150                 155                 160

Arg Arg Asn Thr His Ala Ser Gly Val Ile Pro Gln Ile Ser Leu Val
            165                 170                 175

Val Gly Pro Cys Ala Gly Gly Ala Val Tyr Ser Pro Ala Ile Thr Asp
        180                 185                 190

Phe Thr Val Met Val Asp Gln Thr Ser His Met Phe Ile Thr Gly Pro
    195                 200                 205

Asp Val Ile Lys Thr Val Thr Gly Glu Asp Val Gly Phe Glu Glu Leu
    210                 215                 220

Gly Gly Ala Arg Thr His Asn Ser Thr Ser Gly Val Ala His His Met
225                 230                 235                 240

Ala Gly Asp Glu Lys Asp Ala Val Glu Tyr Val Lys Gln Leu Leu Ser
            245                 250                 255

Tyr Leu Pro Ser Asn Asn Leu Ser Glu Pro Ala Phe Pro Glu Glu
        260                 265                 270

Ala Asp Leu Ala Val Thr Asp Glu Asp Ala Glu Leu Asp Thr Ile Val
    275                 280                 285

Pro Asp Ser Ala Asn Gln Pro Tyr Asp Met His Ser Val Ile Glu His
    290                 295                 300
```

Val Leu Asp Asp Ala Glu Phe Phe Glu Thr Gln Pro Leu Phe Ala Pro
305                 310                 315                 320

Asn Ile Leu Thr Gly Phe Gly Arg Val Glu Gly Arg Pro Val Gly Ile
                325                 330                 335

Val Ala Asn Gln Pro Met Gln Phe Ala Gly Cys Leu Asp Ile Thr Ala
            340                 345                 350

Ser Glu Lys Ala Ala Arg Phe Val Arg Thr Cys Asp Ala Phe Asn Val
        355                 360                 365

Pro Val Leu Thr Phe Val Asp Val Pro Gly Phe Leu Pro Gly Val Asp
    370                 375                 380

Gln Glu His Asp Gly Ile Ile Arg Arg Gly Ala Lys Leu Ile Phe Ala
385                 390                 395                 400

Tyr Ala Glu Ala Thr Val Pro Leu Ile Thr Val Ile Thr Arg Lys Ala
                405                 410                 415

Phe Gly Gly Ala Tyr Asp Val Met Gly Ser Lys His Leu Gly Ala Asp
                420                 425                 430

Leu Asn Leu Ala Trp Pro Thr Ala Gln Ile Ala Val Met Gly Ala Gln
        435                 440                 445

Gly Ala Val Asn Ile Leu His Arg Arg Thr Ile Ala Asp Ala Gly Asp
    450                 455                 460

Asp Ala Glu Ala Thr Arg Ala Arg Leu Ile Gln Glu Tyr Glu Asp Ala
465                 470                 475                 480

Leu Leu Asn Pro Tyr Thr Ala Ala Glu Arg Gly Tyr Val Asp Ala Val
                485                 490                 495

Ile Met Pro Ser Asp Thr Arg Arg His Ile Val Arg Gly Leu Arg Gln
                500                 505                 510

Leu Arg Thr Lys Arg Glu Ser Leu Pro Pro Lys Lys His Gly Asn Ile
        515                 520                 525

Pro Leu
    530

<210> SEQ ID NO 9
<211> LENGTH: 359
<212> TYPE: PRT
<213> ORGANISM: Sulfolobus thuringiensis

<400> SEQUENCE: 9

Met Ile Leu Met Arg Arg Thr Leu Lys Ala Ala Ile Leu Gly Ala Thr
1               5                   10                  15

Gly Leu Val Gly Ile Glu Tyr Val Arg Met Leu Ser Asn His Pro Tyr
            20                  25                  30

Ile Lys Pro Ala Tyr Leu Ala Gly Lys Gly Ser Val Gly Lys Pro Tyr
        35                  40                  45

Gly Glu Val Val Arg Trp Gln Thr Val Gly Gln Val Pro Lys Glu Ile
50                  55                  60

Ala Asp Met Glu Ile Lys Pro Thr Asp Pro Lys Leu Met Asp Asp Val
65                  70                  75                  80

Asp Ile Ile Phe Ser Pro Leu Pro Gln Gly Ala Ala Gly Pro Val Glu
                85                  90                  95

Glu Gln Phe Ala Lys Glu Gly Phe Pro Val Ile Ser Asn Ser Pro Asp
                100                 105                 110

His Arg Phe Asp Pro Asp Val Pro Leu Leu Val Pro Glu Leu Asn Pro
            115                 120                 125

His Thr Ile Ser Leu Ile Asp Glu Gln Arg Lys Arg Arg Glu Trp Lys

```
                130                 135                 140
Gly Phe Ile Val Thr Thr Pro Leu Cys Thr Ala Gln Gly Ala Ala Ile
145                 150                 155                 160

Pro Leu Gly Ala Ile Phe Lys Asp Tyr Lys Met Asp Gly Ala Phe Ile
                165                 170                 175

Thr Thr Ile Gln Ser Leu Ser Gly Ala Gly Tyr Pro Gly Ile Pro Ser
                180                 185                 190

Leu Asp Val Val Asp Asn Ile Leu Pro Leu Gly Asp Gly Tyr Asp Ala
                195                 200                 205

Lys Thr Ile Lys Glu Ile Phe Arg Ile Leu Ser Glu Val Lys Arg Asn
210                 215                 220

Val Asp Glu Pro Lys Leu Glu Asp Val Ser Leu Ala Ala Thr Thr His
225                 230                 235                 240

Arg Ile Ala Thr Ile His Gly His Tyr Glu Val Leu Tyr Val Ser Phe
                245                 250                 255

Lys Glu Glu Thr Ala Ala Glu Lys Val Lys Glu Thr Leu Glu Asn Phe
                260                 265                 270

Arg Gly Glu Pro Gln Asp Leu Lys Leu Pro Thr Ala Pro Ser Lys Pro
                275                 280                 285

Ile Ile Val Met Asn Glu Asp Thr Arg Pro Gln Val Tyr Phe Asp Arg
                290                 295                 300

Trp Ala Gly Asp Ile Pro Gly Met Ser Val Val Val Gly Arg Leu Lys
305                 310                 315                 320

Gln Val Asn Lys Arg Met Ile Arg Leu Val Ser Leu Ile His Asn Thr
                325                 330                 335

Val Arg Gly Ala Ala Gly Gly Ile Leu Ala Ala Glu Leu Leu Val
                340                 345                 350

Glu Lys Gly Tyr Ile Glu Lys
                355

<210> SEQ ID NO 10
<211> LENGTH: 314
<212> TYPE: PRT
<213> ORGANISM: Metallosphaera sedula

<400> SEQUENCE: 10

Met Thr Glu Lys Val Ser Val Val Gly Ala Gly Val Ile Gly Val Gly
1               5                   10                  15

Trp Ala Thr Leu Phe Ala Ser Lys Gly Tyr Ser Val Ser Leu Tyr Thr
                20                  25                  30

Glu Lys Lys Glu Thr Leu Asp Lys Gly Ile Glu Lys Leu Arg Asn Tyr
                35                  40                  45

Val Gln Val Met Lys Asn Asn Ser Gln Ile Thr Glu Asp Val Asn Thr
50                  55                  60

Val Ile Ser Arg Val Ser Pro Thr Thr Asn Leu Asp Glu Ala Val Arg
65                  70                  75                  80

Gly Ala Asn Phe Val Ile Glu Ala Val Ile Glu Asp Tyr Asp Ala Lys
                85                  90                  95

Lys Lys Ile Phe Gly Tyr Leu Asp Ser Val Leu Asp Lys Glu Val Ile
                100                 105                 110

Leu Ala Ser Ser Thr Ser Gly Leu Leu Ile Thr Glu Val Gln Lys Ala
                115                 120                 125

Met Ser Lys His Pro Glu Arg Ala Val Ile Ala His Pro Trp Asn Pro
130                 135                 140
```

Pro His Leu Leu Pro Leu Val Glu Ile Val Pro Gly Glu Lys Thr Ser
145                 150                 155                 160

Met Glu Val Val Glu Arg Thr Lys Ser Leu Met Glu Lys Leu Asp Arg
                165                 170                 175

Ile Val Val Leu Lys Lys Glu Ile Pro Gly Phe Ile Gly Asn Arg
            180                 185                 190

Leu Ala Phe Ala Leu Phe Arg Glu Ala Val Tyr Leu Val Asp Glu Gly
                195                 200                 205

Val Ala Thr Val Glu Asp Ile Asp Lys Val Met Thr Ala Ala Ile Gly
            210                 215                 220

Leu Arg Trp Ala Phe Met Gly Pro Phe Leu Thr Tyr His Leu Gly Gly
225                 230                 235                 240

Gly Glu Gly Gly Leu Glu Tyr Phe Phe Asn Arg Gly Phe Gly Tyr Gly
                245                 250                 255

Ala Asn Glu Trp Met His Thr Leu Ala Lys Tyr Asp Lys Phe Pro Tyr
                260                 265                 270

Thr Gly Val Thr Lys Ala Ile Gln Gln Met Lys Glu Tyr Ser Phe Ile
            275                 280                 285

Lys Gly Lys Thr Phe Gln Glu Ile Ser Lys Trp Arg Asp Glu Lys Leu
290                 295                 300

Leu Lys Val Tyr Lys Leu Val Trp Glu Lys
305                 310

<210> SEQ ID NO 11
<211> LENGTH: 659
<212> TYPE: PRT
<213> ORGANISM: Sulfolobus tokodaii

<400> SEQUENCE: 11

Met Thr Glu Lys Leu Ser Glu Gln Leu Gln Gln Leu Gly Glu Gln Asn
1               5                   10                  15

Leu Glu Glu Lys Ala Asp Tyr Asn Met Arg Tyr Tyr Lys Tyr Leu Tyr
                20                  25                  30

Lys Lys Ser Ile Glu Glu Pro Asp Lys Phe Trp Gly Glu Leu Ala Glu
            35                  40                  45

Glu Leu Ile Thr Trp Tyr Glu Pro Trp Lys Gln Ala Phe Val Gln Glu
50                  55                  60

Glu Gly Leu Leu Thr Lys Trp Phe Val Gly Gly Lys Leu Asn Ala Ser
65                  70                  75                  80

Tyr Asn Ala Val Asp Arg His Leu Asn Ser His Arg Lys Tyr Lys Ala
                85                  90                  95

Ala Ile Phe Trp Glu Ser Glu Lys Gly Glu Lys Lys Val Val Thr Tyr
            100                 105                 110

Gln Asp Leu Phe Tyr Glu Val Asn Lys Trp Ala Asn Ala Leu Arg Glu
        115                 120                 125

Leu Gly Val Lys Lys Gly Asp Arg Val Thr Ile Tyr Met Pro Leu Thr
    130                 135                 140

Pro Glu Gly Val Ile Ala Lys Leu Ala Val Ala Arg Leu Gly Ala Ile
145                 150                 155                 160

His Ser Val Val Phe Ala Gly Phe Gly Ala Gln Ala Leu Ala Asp Arg
                165                 170                 175

Ile Ala Asp Ala Gly Ala Lys Val Val Ile Thr Ala Asp Ala Tyr Tyr
            180                 185                 190

Arg Arg Gly Lys Leu Val Glu Leu Lys Lys Thr Val Asp Glu Ala Leu
        195                 200                 205

```
Asn Ile Leu Gly Asp Lys Ser Pro Val Gln Lys Val Leu Val Tyr Lys
    210                 215                 220

Arg Thr Gly Thr Glu Ile Pro Phe Lys Glu Gly Arg Asp Val Tyr Phe
225                 230                 235                 240

Asp Glu Val Gly Lys Tyr Lys Tyr Ile Glu Pro Val Pro Val Glu Ala
                245                 250                 255

Thr Glu Pro Leu Phe Ile Leu Tyr Thr Ser Gly Thr Thr Gly Lys Pro
                260                 265                 270

Lys Gly Ile Val His Ser Thr Gly Gly Tyr Leu Val Gly Thr Ala Val
            275                 280                 285

Met Leu Leu Trp Ser Tyr Gly Leu Ser Gln Glu Asn Asp Val Leu Phe
    290                 295                 300

Asn Thr Ser Asp Ile Gly Trp Ile Val Gly His Ser Tyr Ile Thr Tyr
305                 310                 315                 320

Ser Pro Leu Val Met Gly Arg Ser Ile Val Ile Tyr Glu Ser Ala Pro
                325                 330                 335

Asp Tyr Pro Tyr Pro Asp Lys Trp Ala Glu Met Ile Glu Lys Tyr Arg
                340                 345                 350

Ala Thr Thr Phe Gly Thr Ser Ala Thr Ala Ile Arg Thr Leu Met Lys
            355                 360                 365

Tyr Gly Glu Asp Tyr Val Lys Gln His Asp Leu Ser Ser Leu Arg Ile
    370                 375                 380

Ile Val Thr Asn Gly Glu Pro Leu Asn Tyr Ala Pro Trp Lys Trp Gly
385                 390                 395                 400

Leu Glu Val Val Gly Gly Lys Val Phe Met Ser His Gln Trp Trp
                405                 410                 415

Gln Thr Glu Thr Gly Gly Pro Asn Ile Gly Tyr Ile Pro Gly Val Val
            420                 425                 430

Tyr Leu Pro Met Lys Ser Gly Pro Ala Val Gly Phe Ala Leu Pro Gly
    435                 440                 445

Asn Lys Val Thr Val Asn Glu Glu Gly Lys Glu Thr Lys Pro Arg
450                 455                 460

Glu Arg Gly Tyr Leu Val Met Leu Pro Pro Phe Pro Pro Met Met Met
465                 470                 475                 480

Ile Gly Met Trp Asn Asp Pro Asp Asn Glu Arg Leu Lys Lys Thr Tyr
                485                 490                 495

Phe Ser Lys Phe Pro Gly Ile Tyr Tyr Pro Gly Asp Tyr Ala Met Ile
            500                 505                 510

Asp Glu Asp Gly Tyr Ile Trp Val Met Gly Arg Ala Asp Glu Thr Ile
    515                 520                 525

Lys Val Ala Ala His Arg Ile Gly Ala Gly Val Glu Ser Ile Val
530                 535                 540

Thr Ser His Pro Ala Val Ala Glu Ala Ala Val Gly Ile Pro Asp
545                 550                 555                 560

Pro Val Lys Gly Glu Ala Val His Leu Phe Val Leu Lys Val Gly
                565                 570                 575

Tyr Lys Pro Ser Pro Gln Leu Ala Arg Glu Ile Gln Glu His Val Arg
            580                 585                 590

Lys Tyr Met Gly Ala Ile Val Thr Pro Glu Val His Phe Val Asp Lys
    595                 600                 605

Leu Pro Lys Thr Arg Ser Gly Lys Ile Met Arg Arg Val Ile Lys Ala
    610                 615                 620
```

Val Met Met Gly Gln Ser Ala Gly Asp Ile Thr Thr Leu Glu Asp Glu
625                 630                 635                 640

Ala Ser Met Asp Glu Ile Lys Lys Ala Val Glu Glu Phe Lys Lys Ser
            645                 650                 655

Leu Ser Gln

<210> SEQ ID NO 12
<211> LENGTH: 259
<212> TYPE: PRT
<213> ORGANISM: Metallosphaera sedula

<400> SEQUENCE: 12

Met Glu Phe Glu Thr Ile Glu Thr Lys Lys Glu Gly Asn Leu Phe Trp
1               5                   10                  15

Ile Thr Leu Asn Arg Pro Asp Lys Leu Asn Ala Leu Asn Ala Lys Leu
            20                  25                  30

Leu Glu Glu Leu Asp Arg Ala Val Ser Gln Ala Glu Ser Asp Pro Glu
        35                  40                  45

Ile Arg Val Ile Ile Ile Thr Gly Lys Gly Lys Ala Phe Cys Ala Gly
    50                  55                  60

Ala Asp Ile Thr Gln Phe Asn Gln Leu Thr Pro Ala Glu Ala Trp Lys
65                  70                  75                  80

Phe Ser Lys Lys Gly Arg Glu Ile Met Asp Lys Ile Glu Ala Leu Ser
                85                  90                  95

Lys Pro Thr Ile Ala Met Ile Asn Gly Tyr Ala Leu Gly Gly Gly Leu
            100                 105                 110

Glu Leu Ala Leu Ala Cys Asp Ile Arg Ile Ala Ala Glu Glu Ala Gln
        115                 120                 125

Leu Gly Leu Pro Glu Ile Asn Leu Gly Ile Tyr Pro Gly Tyr Gly Gly
    130                 135                 140

Thr Gln Arg Leu Thr Arg Val Ile Gly Lys Gly Arg Ala Leu Glu Met
145                 150                 155                 160

Met Met Thr Gly Asp Arg Ile Pro Gly Lys Asp Ala Glu Lys Tyr Gly
                165                 170                 175

Leu Val Asn Arg Val Val Pro Leu Ala Asn Leu Glu Gln Glu Thr Arg
            180                 185                 190

Lys Leu Ala Glu Lys Ile Ala Lys Lys Ser Pro Ile Ser Leu Ala Leu
        195                 200                 205

Ile Lys Glu Val Val Asn Arg Gly Leu Asp Ser Pro Leu Leu Ser Gly
    210                 215                 220

Leu Ala Leu Glu Ser Val Gly Trp Gly Val Val Phe Ser Thr Glu Asp
225                 230                 235                 240

Lys Lys Glu Gly Val Ser Ala Phe Leu Glu Lys Arg Glu Pro Thr Phe
                245                 250                 255

Lys Gly Lys

<210> SEQ ID NO 13
<211> LENGTH: 334
<212> TYPE: PRT
<213> ORGANISM: Sulfolobus tokodaii

<400> SEQUENCE: 13

Met Lys Ala Ile Val Val Pro Gly Pro Lys Gln Gly Tyr Lys Leu Glu
1               5                   10                  15

Glu Val Pro Asp Pro Lys Pro Gly Lys Asp Glu Val Ile Ile Arg Val
            20                  25                  30

```
Asp Arg Ala Ala Leu Cys Tyr Arg Asp Leu Leu Gln Leu Gln Gly Tyr
        35              40              45

Tyr Pro Arg Met Lys Tyr Pro Val Ile Leu Gly His Glu Val Val Gly
50              55              60

Thr Ile Glu Glu Val Gly Glu Asn Ile Lys Gly Phe Glu Val Gly Asp
65              70              75              80

Lys Val Ile Ser Leu Leu Tyr Ala Pro Asp Gly Thr Cys Glu Tyr Cys
            85              90              95

Gln Ile Gly Glu Glu Ala Tyr Cys His His Arg Leu Gly Tyr Ser Glu
            100             105             110

Glu Leu Asp Gly Phe Phe Ala Glu Lys Ala Lys Ile Lys Val Thr Ser
        115             120             125

Leu Val Lys Val Pro Lys Gly Thr Pro Asp Glu Gly Ala Val Leu Val
        130             135             140

Pro Cys Val Thr Gly Met Ile Tyr Arg Gly Ile Arg Arg Ala Gly Gly
145             150             155             160

Ile Arg Lys Gly Glu Leu Val Leu Val Thr Gly Ala Ser Gly Gly Val
            165             170             175

Gly Ile His Ala Ile Gln Val Ala Lys Ala Leu Gly Ala Lys Val Ile
            180             185             190

Gly Val Thr Thr Ser Glu Glu Lys Ala Lys Ile Ile Lys Gln Tyr Ala
        195             200             205

Asp Tyr Val Ile Val Gly Thr Lys Phe Ser Glu Glu Ala Lys Lys Ile
        210             215             220

Gly Asp Val Thr Leu Val Ile Asp Thr Val Gly Thr Pro Thr Phe Asp
225             230             235             240

Glu Ser Leu Lys Ser Leu Trp Met Gly Gly Arg Ile Val Gln Ile Gly
            245             250             255

Asn Val Asp Pro Ser Gln Ile Tyr Asn Leu Arg Leu Gly Tyr Ile Ile
            260             265             270

Leu Lys Asp Leu Lys Ile Val Gly His Ala Ser Ala Thr Lys Lys Asp
        275             280             285

Ala Glu Asp Thr Leu Lys Leu Thr Gln Glu Gly Lys Ile Lys Pro Val
        290             295             300

Ile Ala Gly Thr Val Ser Leu Glu Asn Ile Asp Glu Gly Tyr Lys Met
305             310             315             320

Ile Lys Asp Lys Asn Lys Val Gly Lys Val Leu Val Lys Pro
            325             330
```

PRODUCING A TRIMETHYLPENTANOIC ACID USING HYBRID POLYKETIDE SYNTHASES

CROSS-REFERENCE TO RELATED APPLICATIONS

This application claims priority to U.S. Provisional Patent Application Ser. No. 61/416,133, filed Nov. 22, 2010, which is hereby incorporated by reference.

STATEMENT OF GOVERNMENTAL SUPPORT

This invention was made with government support under Contract No. DE-AC02-05CH11231 awarded by the U.S. Department of Energy and Award No. 0540879 awarded by the National Science Foundation. The government has certain rights in the invention.

FIELD OF THE INVENTION

This invention relates generally to iso-octane production using polyketide synthases.

BACKGROUND OF THE INVENTION

Iso-octane (such as 2,2,4-trimethylpentane) is one of the most important components in gasoline and is the gasoline component for which the octane rating has been coined. While gasoline has many other components, fuels for piston engine airplanes can be pure iso-octane. The branches in iso-octane give it the appropriate combustion properties for ignition engines. Unfortunately, the branches in iso-octane also make it nearly impossible to produce biologically. Indeed, tertiary butyl carbons exist rarely in nature. The biological production of iso-octane and molecules like it would be extremely valuable to the transportation fuels industry as it would allow direct substitution of these biofuels into the existing transportation and refining infrastructure.

SUMMARY OF THE INVENTION

The present invention provides for a polyketide synthase (PKS), capable of synthesizing a trimethylpentanoic acid. The PKS is not a naturally occurring PKS. In some embodiments of the invention, the PKS is a hybrid PKS comprising modules, domains, and/or portions thereof from two or more naturally occurring PKSs. The present invention provides for a recombinant nucleic acid that encodes a polyketide synthase (PKS) of the present invention. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present invention. The present invention provides for a host cell comprising any of the recombinant nucleic acid and/or PKS of the present invention. In some embodiments, the host cell, when cultured under a suitable condition, is capable of producing the trimethylpentanoic acid.

The present invention provides for a host cell comprising any of the recombinant nucleic acid and/or PKS of the present invention. In some embodiments, the host cell, when cultured, is capable of producing a trimethylpentanoic acid. In some embodiments of the invention, the host cell carries a number of genes that enable the production of 2-methylmalonyl-CoA, a necessary precursor of trimethypentanoic acid biosynthesis.

The present invention provides a method of producing a trimethylpentanoic acid, comprising: providing a host cell of the present invention, and culturing said host cell in a suitable culture medium such that the trimethylpentanoic acid is produced. The method can further comprise isolating the trimethylpentanoic acid, and optionally, reducing the isolated trimethylpentanoic acid into a trimethylpentanol or an iso-octane.

The present invention provides for a composition comprising a trimethylpentanoic acid isolated from a host cell from which the trimethylpentanoic acid was produced, and trace residues and/or contaminants of the host cell. Such trace residues and/or contaminants include cellular material produced by the lysis of the host cell. In some embodiments of the invention, the trace residues and/or contaminants do not or essentially do not interfere or retard any further reaction involving the trimethylpentanoic acid.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figure 1:
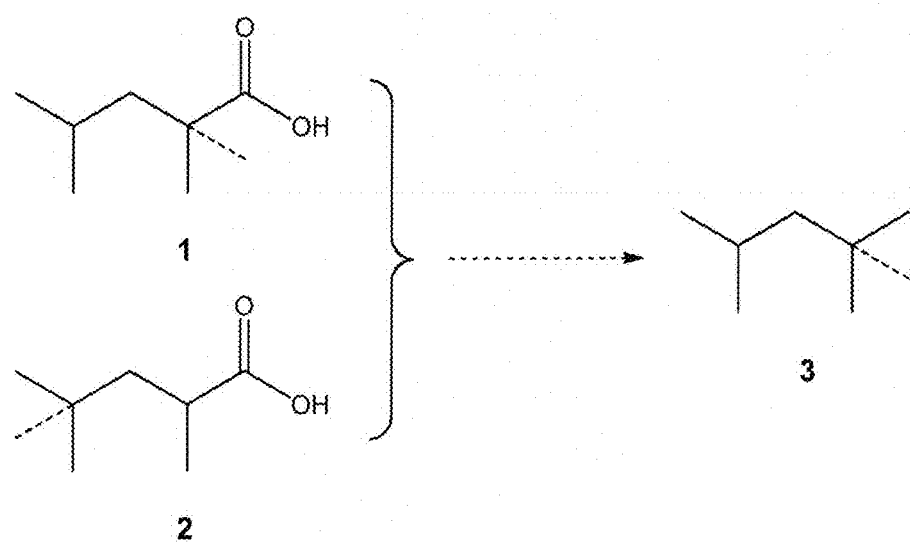
FIG. 1 shows two routes to production of iso-octane provided by the invention.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a PKS" includes a plurality of such PKSs, and so forth.

The term "Ave" refers to Avermectin.
The term "But" refers to Butyrolactol A.
The term "Ery" refers to Erythromycin.
The term "DEBS" refers to the Ery PKS.
The term "Nan" refers to Nanchangmycin.
The term "Lip" refers to Lipomycin.

The term "functional variant" describes an enzyme that has a polypeptide sequence that is at least 70%, 75%, 80%, 85%, 90%, 95% or 99% identical to any one of the enzymes described herein. The "functional variant" enzyme may retain amino acids residues that are recognized as conserved for the enzyme, and may have non-conserved amino acid residues substituted or found to be of a different amino acid, or amino acid(s) inserted or deleted, but which does not affect or has insignificant effect its enzymatic activity as compared to the enzyme described herein. The "functional variant" enzyme has an enzymatic activity that is identical or essentially identical to the enzymatic activity of the enzyme described herein. The "functional variant" enzyme may be found in nature or be an engineered mutant thereof.

These and other objects, advantages, and features of the invention will become apparent to those persons skilled in the art upon reading the details of the invention as more fully described below.

Polyketide Synthases (PKS)

The present invention provides for a polyketide synthase (PKS) capable of synthesizing a trimethyl pentanoic acid. The PKS is not a naturally occurring PKS. In some embodiments of the invention, the PKS is a hybrid PKS comprising modules, domains, and/or portions thereof from two or more PKSs. In some embodiments of the invention, the trimethyl pentanoic acid is 2,2,4-trimethyl pentanoic acid or 2,4,4-trimethyl pentanoic acid.

Complex polyketides comprise a large class of natural products that are synthesized in bacteria (mainly members actinomycete family; e.g. *Streptomyces*), fungi and plants. Polyketides form the aglycone component of a large number of clinically important drugs, such as antibiotics (e.g. erythromycin, tylosin), antifungal agents (e.g. nystatin), anticancer agents (e.g. epothilone), immunosuppressives (e.g. rapamycin), etc. Though these compounds do not resemble each other either in their structure or their mode of action, they share a common basis for their biosynthesis, which is carried out by a group of enzymes designated polyketide synthases.

Polyketide synthases (PKS) employ short chain fatty acyl-CoAs in Claisen condensation reactions to produce polyketides. Unlike fatty acid synthases which utilize acetyl CoA as the starter and malonyl-CoA as the extender units, and use a single module iteratively to produce the nascent acyl chains, PKSs are composed of discrete modules, each catalyzing the chain growth of a single step. Modules can differ from each other in composition so that overall, a number of different starters (e.g. acetyl-CoA, propionyl-CoA, isobutyryl-CoA) and extenders, some of which contain stereospecific methyl (or ethyl) side chains can be incorporated. In addition, PKS modules do not always reduce the 3-carbonyl formed from condensation but may leave it either unreduced (ketone), partially reduced (hydroxyl, 2,3-ene) or fully reduced (3-methylene). Many polyketide synthases employ malonyl-CoA or [S]-2-methylmalonyl-CoA as the starter for polyketide synthesis. In such cases the terminal carboxyl group is usually removed by a decarboxylase domain present at the N-terminus of the corresponding loading domain of the PKS. In summary, the structure (and chirality) of the α-carbon and β-carbonyl is determined by the module of the PKS employed in the synthesis of the growing chain at each particular step. Because of the correspondence between use of modules in the synthesis and the structure of the polyketide produced, it is possible to program the synthesis to produce a compound of desired structure by selection and genetic manipulation of polyketide synthases.

All extender modules carry the β-acyl ACP synthase (commonly called the ketosynthase or KS) domain, which conducts the decarboxylative condensation step between the extender and the growing polyketide chain, and the acyl carrier protein (ACP) domain that carries the growing acyl chain and presents it to the cognate reductive domains for reduction of the β-carbonyl. Modules can differ from each other in composition so that a number of different starter and extender units, some of which contain stereospecific side chains (e.g. methyl, ethyl, propylene) can be incorporated. The acyltransferase (AT) domain of each module determines the extender unit (e.g. malonyl-CoA, methylmalonyl-CoA, etc.) incorporated. In addition, PKS modules do not always reduce the β-carbonyl formed from condensation but may leave it either unreduced (ketone), partially reduced (hydroxyl, 2,3-ene) or fully reduced (3-methylene), as shown in FIG. 2. The ketoreductase (KR) domain reduces the ketone to the OH function (stereospecifically); the dehydratase (DH) domain removes water from the α and β carbons leaving an α,β trans-double bond; the enoylreductase (ER) domain reduces the double bond to a β-methylene center; the reductive state of the β-carbonyl, therefore, is determined by the presence of functional reductive domains in the corresponding module. Less commonly, modules are found to contain an additional C-methylation domain (yielding an additional α-methyl side chain, as in epothilone). The makeup of the PKS, therefore, determines the choice of starter and extender acyl units incorporated, the extent of reduction at each condensation step, and the total number of units added to the chain. The wide diversity of structures of polyketides seen in nature is attributed to the diversity in PKS compositions.

A partial list of sources of PKS sequences that can be used in making the PKSs of the present invention, for illustration and not limitation, includes Ambruticin (U.S. Pat. No. 7,332, 576); Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FRO008) (Hu et al., 1994, Mol. Microbiol. 14: 163-72); Epothilone (U.S. Pat. No. 6,303,342); Erythromycin (WO 93/13663; U.S. Pat. No. 5,824,513; Donadio et al., 1991, Science 252:675-79; Cortes et al., 1990, Nature 348:176-8); FK506 (Motamedi et al., 1998, Eur. J. Biochem. 256:528-34; Motamedi et al., 1997, Eur. J. Biochem. 244:74-80); FK520 or ascomycin (U.S. Pat. No. 6,503,737; see also Nielsen et al., 1991, Biochem. 30:5789-96); Jerangolid (U.S. Pat. No. 7,285,405); Leptomycin (U.S. Pat. No. 7,288,396); Lovastatin (U.S. Pat. No. 5,744,350); Nanchangmycin (Sun et al., 2002, Microbiology, 148: 361-71; Nemadectin (Mac-Neil et al., 1993, supra); Niddamycin (Kakavas et al., 1997, J. Bacteriol. 179:7515-22); Oleandomycin (Swan et al., 1994, Mol. Gen. Genet. 242:358-62; U.S. Pat. No. 6,388,099; Olano et al., 1998, Mol. Gen. Genet. 259:299-308); Pederin (PCT publication no. WO 2003/044186); Pikromycin (Xue et al., 2000, Gene 245:203-211); Pimaricin (PCT publication no. WO 2000/077222); Platenolide (EP Pat. App. 791,656); Rapamycin (Schwecke et al., 1995, Proc. Natl. Acad. Sci. USA 92:7839-43); Aparicio et al., 1996, Gene 169:9-16); Rifamycin (August et al., 1998, Chemistry & Biology, 5: 69-79); Soraphen (U.S. Pat. No. 5,716,849; Schupp et al., 1995, J. Bacteriology 177: 3673-79); Spiramycin (U.S. Pat. No. 5,098,837); Tylosin (EP 0 791,655; Kuhstoss et al., 1996, Gene 183:231-36; U.S. Pat. No. 5,876,991). Additional suitable PKS coding sequences are readily available to one skilled in the art, or remain to be discovered and characterized, but will be available to those of skill (e.g., by reference to GenBank). Each of the references cited is hereby specifically and individually incorporated by reference.

Of the more than thirty PKSs examined, the correspondence between use of modules in the biosynthesis and the structure of the polyketide produced is fully understood both at the level of the protein sequence of the PKS and the DNA sequence of the corresponding genes. The programming of modules into polyketide structure can be identified by sequence determination. It is possible to clone (or synthesize) DNA sequences corresponding to desired modules and transfer them as fully functioning units to heterologous, otherwise non-polyketide producing hosts such as *E. coli* (B. A. Pfeifer, S. J. Admiraal, H. Gramajo, D. E. Cane, C. Khosla, *Science* 291, 1790 (2001); hereby incorporated by reference) and *Streptomyces* (C. M. Kao, L. Katz, C. Khosla, *Science* 265, 509 (1994); hereby incorporated by reference). Additional genes employed for polyketide biosynthesis have also been identified. Genes that determine phosphopantetheine:protein transferase (PPTase) that transfer the 4-phosphopantetheine co-factor of the ACP domains, commonly present in polyketide producing hosts, have been cloned in *E. coli* and other hosts (K. J. Weissman, H. Hong, M. Oliynyk, A. P. Siskos, P. F. Leadlay, *Chembiochem* 5, 116 (2004); hereby incorporated by reference). It is also possible to re-program polyketide biosynthesis to produce a compound of desired structure by either genetic manipulation of a single PKS or by construction of a hybrid PKS composed of modules from two or more sources (K. J. Weissman, H. Hong, M. Oliynyk, A. P. Siskos, P. F. Leadlay, *Chembiochem* 5, 116 (2004); hereby incorporated by reference).

Recombinant methods for manipulating modular PKS genes are described in U.S. Pat. Nos. 5,672,491; 5,843,718; 5,830,750; 5,712,146; and 6,303,342; and in PCT publication nos. WO 98/49315 and WO 97/02358; hereby incorporated by reference. A number of genetic engineering strategies have been used with various PKSs to demonstrate that the structures of polyketides can be manipulated to produce novel polyketides (see the patent publications referenced supra and Hutchinson, 1998, *Curr. Opin. Microbiol.* 1:319-329, and Baltz, 1998, Trends Microbiol. 6:76-83; hereby incorporated by reference). In some embodiments, the components of the hybrid PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication no. WO 00/47724, hereby incorporated by reference.

TEs capable of releasing free acids as described here include the TE of the eryPKS and MonCII from the monensin pathway in *Streptomyces cinnamonensis*. The vast number of polyketide pathways that have been elucidated provide a host of different options to produce the desired products as well as the large number of derivatives. The exact interfaces between non-cognate enzyme partners will be determined on a case-by-case basis. ACP-linker-KS and ACP-linker-TE regions from the proteins of interest will be aligned to examine the least disruptive fusion point for the hybrid synthase. Genetic constructions will employ sequence and ligation independent cloning (SLIC) so as to eliminate the incorporation of genetic "scarring".

In some embodiments of the invention, the polyketide synthase (PKS) is capable of synthesizing 2,2,4-trimethylpentanoic acid (compound 1, FIG. 1) and the PKS comprises a loading module capable of using isobutyryl-CoA as a starter unit, and a module capable of extending using 2-methylmalonyl-CoA as an extending unit. In some embodiments of the invention, the loading module capable of using isobutyryl-CoA as a starter unit comprises $AT_L$ and $ACP_L$ of Ave Load-Mod1. In some embodiments of the invention, the module capable of extending using 2-methylmalonyl-CoA as an extending unit comprises KS and mmAT of Ave Load-Mod1, DH, ER, and KR of DEBS Mod4 or Nan Mod2, a cMT domain, an ACP and a TE. In some embodiments of the invention, the PKS comprises the structure depicted in FIG. 2A or FIG. 2B.

In some embodiments of the invention, the polyketide synthase (PKS) is capable of synthesizing 2,4,4-tri compound 2 and the PKS comprises a loading module capable of using pivaloyl-CoA as a starter unit, and a module capable of extending using 2-methylmalonyl-CoA as an extending unit. In some embodiments of the invention, the loading module capable of using pivaloyl-CoA as a starter unit comprises $AT_L$ and $ACP_L$ of Ave Load-Mod1. In some embodiments of the invention, the module capable of extending using 2-methylmalonyl-CoA as an extending unit comprises KS and mmAT of Ave Load-Mod1, and DH, ER, KR, ACP and TE of DEBS Mod4-TE or Nan Mod2-TE. In some embodiments of the invention, the PKS comprises one of the structures depicted in FIG. 3.

In some embodiments of the invention, the polyketide synthase (PKS) is capable of synthesizing compound 1 and the PKS comprises a loading module capable of using isobutyryl-CoA as a starter unit, a module capable of extending using 2-methylmalonyl-CoA as an extending unit, and a TE. In some embodiments of the invention, the loading module capable of using isobutyryl-CoA as a starter unit comprises $AT_L$, $ACP_L$ and KS1 of Lipomycin Load Module. In some embodiments of the invention, the module capable of extending using 2-methylmalonyl-CoA as an extending unit comprising the following modules: mmAT, DH, ER, KR, cMT, and ACP. The mmAT can be the mmAT of Ave Load-Mod1. The DH, ER, KR can be DEBS Mod4 or Nan Mod2. The cMT domain can be any suitable cMT. The TE can be any suitable TE, such as an Ery TE. In some embodiments of the invention, the PKS comprises the structure depicted in FIG. 2C or FIG.

Figure 2A:
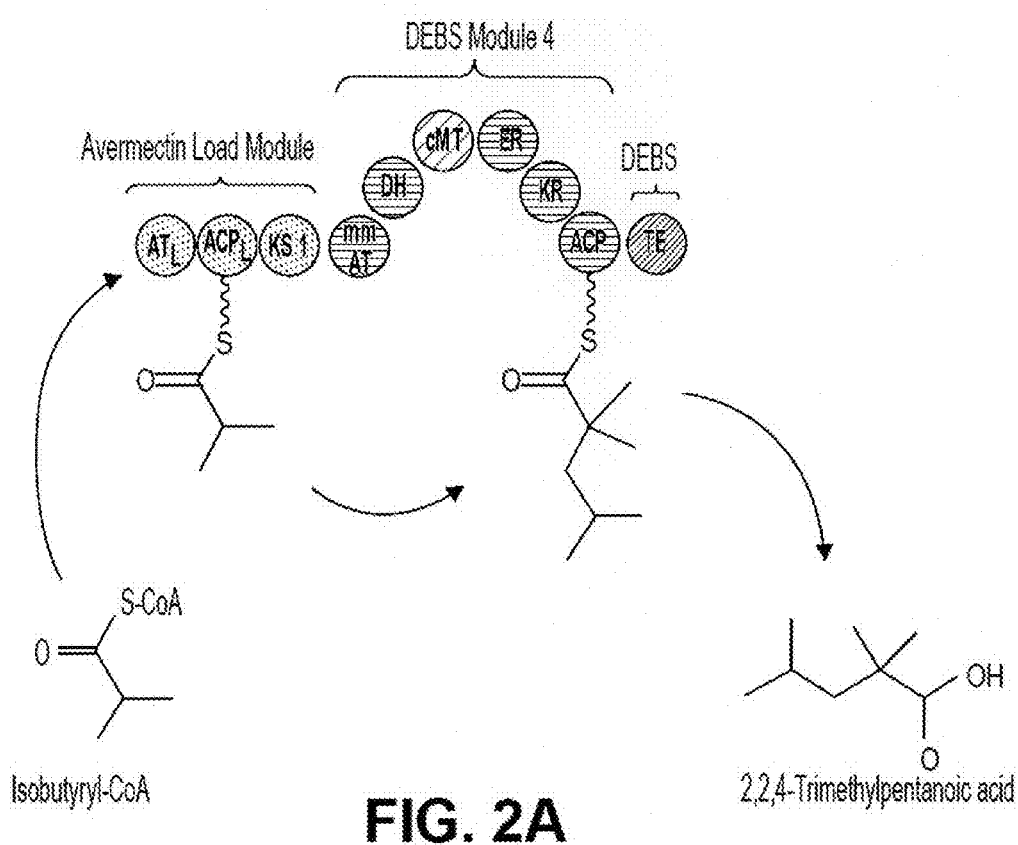
FIG. 2 shows four examples of PKS-A constructs, each designed to produce 2,2,4-trimethylpentanoic acid provided by the invention.
Figure 2B:
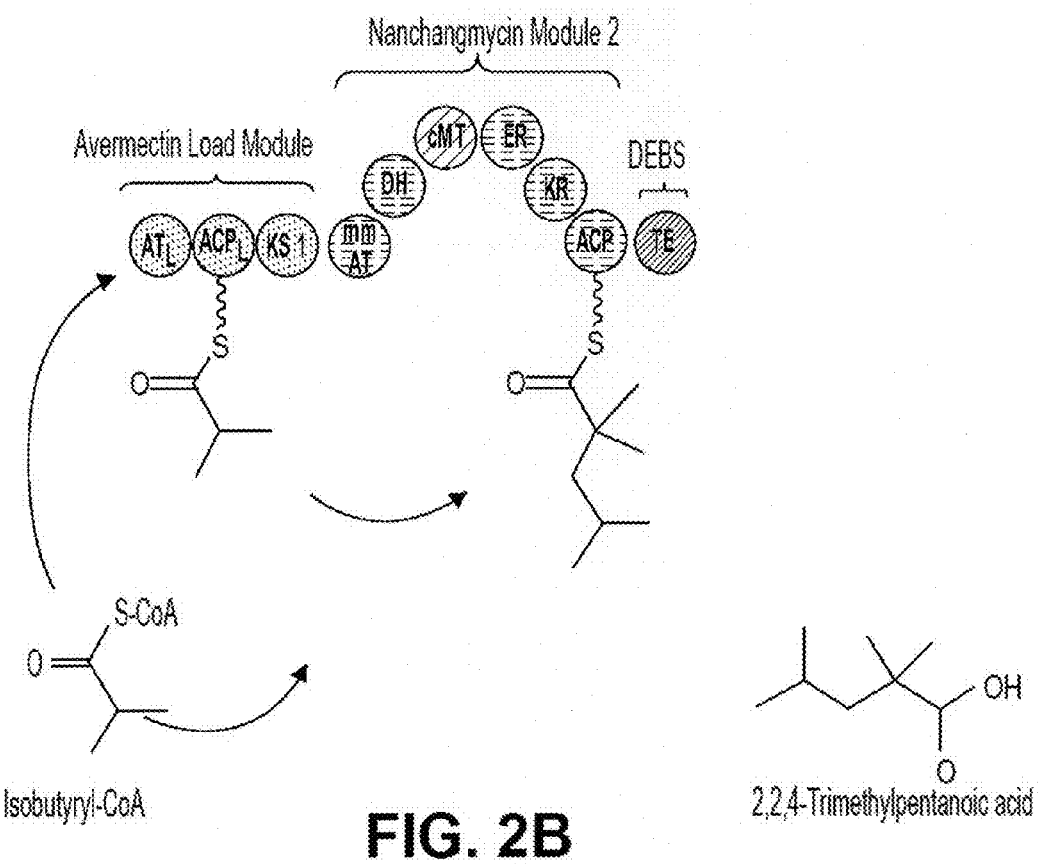
Figure 2C:
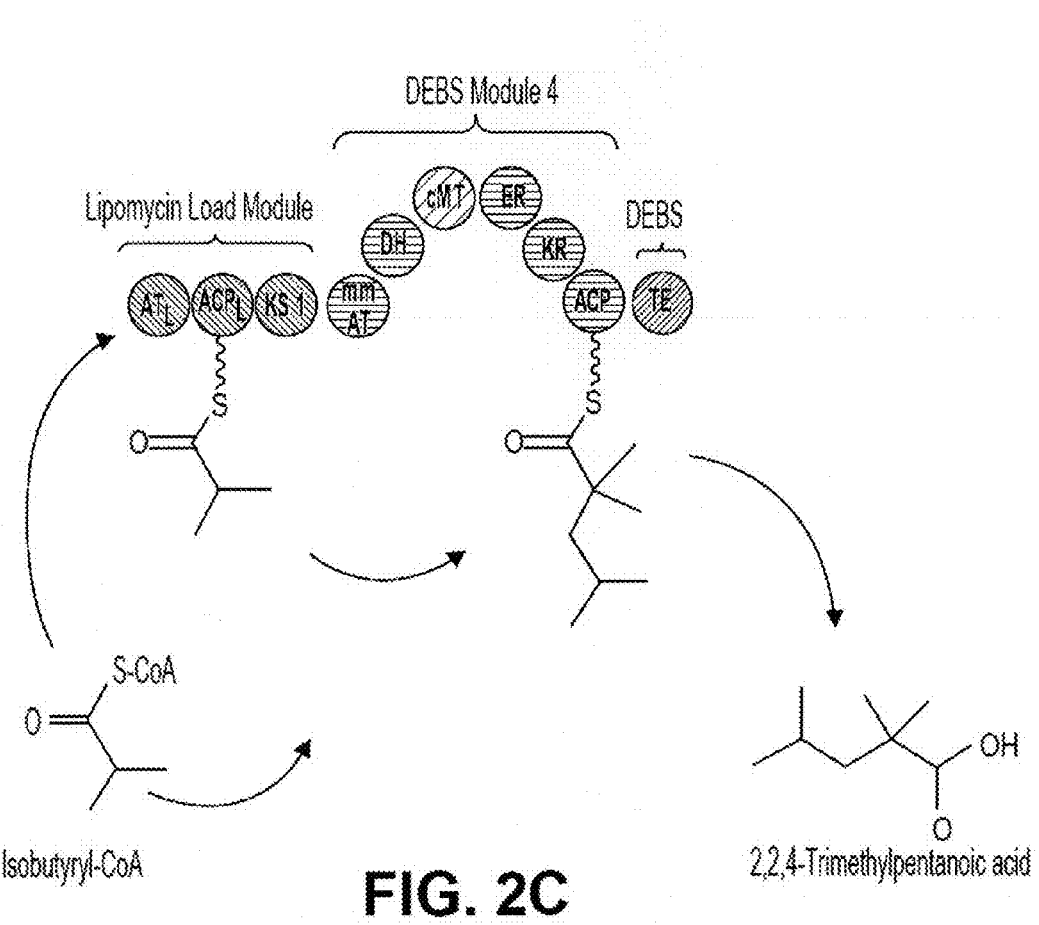
Figure 2D:
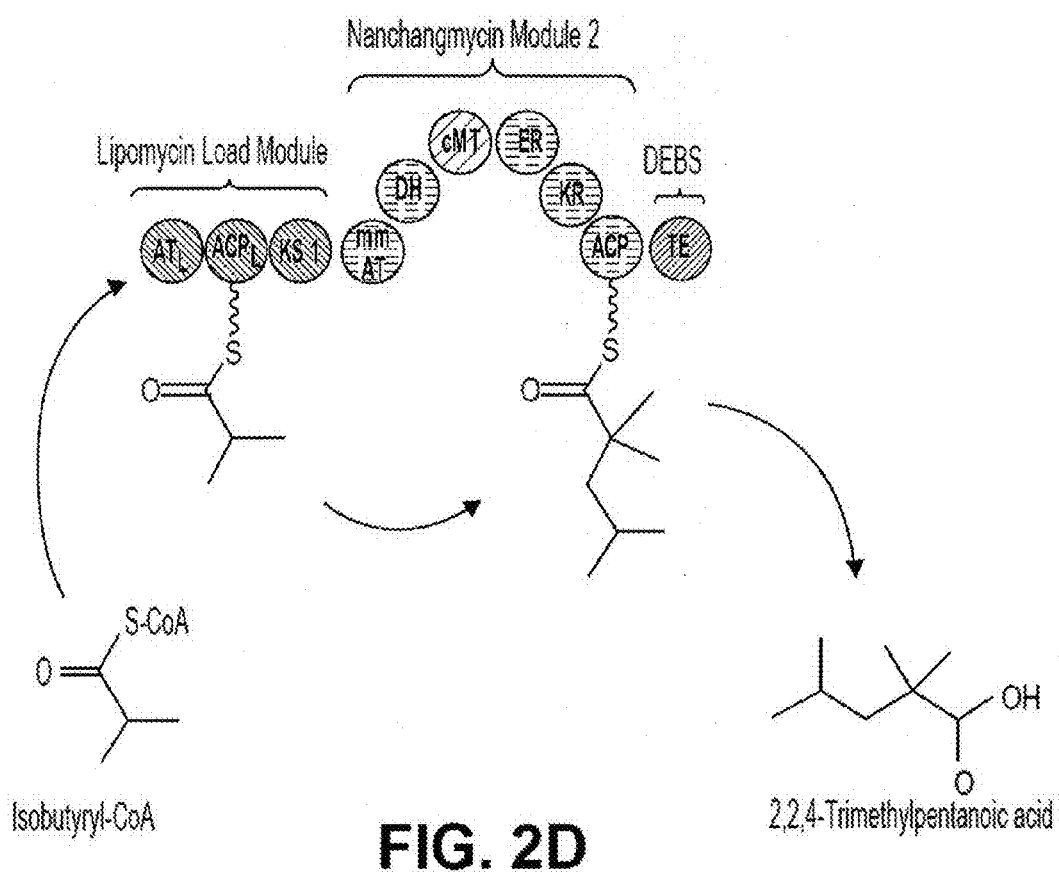

2D. In a particular embodiment, the KS domain of module 1 is the KS domain that is immediately downstream of the ACP domain of the loading module. For example, as shown in FIG. 2A or FIG. 2B, if the loading module is from the ave PKS, the KS domain of module 1 is from module 1 of the ave PKS. The region between the ACP of the loading module and the KS1 domain is therefore preserved as in the natural PKS to ensure that both the contact between the two ACP and KS domains and the transfer of the isobutyryl moiety from ACP to KS is maintained, as in the natural system.

In some embodiments of the invention, the polyketide synthase (PKS) is capable of synthesizing compound 2 and the PKS comprises a loading module capable of using pivaloyl-CoA as a starter unit, a module capable of extending using 2-methylmalonyl-CoA as an extending unit, and a TE. In some embodiments of the invention, the loading module capable of using pivaloyl-CoA as a starter unit comprises $AT_L$, $ACP_L$ and KS1 of Ave Load-Mod 1. In other embodiments of the invention, the loading module capable of using pivaloyl-CoA as a starter unit comprises $AT_L$, $ACP_L$ and KS1 of But Load Module of *Streptomyces rochei*. In some embodiments of the invention, the module capable of extending using 2-methylmalonyl-CoA as an extending unit comprises mmAT of Ave Load-Mod 1, and DH, ER, KR, ACP of Ery Mod4. The TE can be any suitable TE, such as an Ery TE. In some embodiments of the invention, the PKS comprises the structure depicted in FIG. 3A or FIG. 3B.

In some embodiments of the invention, the polyketide synthase (PKS) is capable of synthesizing compound 2 and the PKS comprises a loading module capable of using isobutyryl-CoA as a starter unit, a module capable of extending using 2-methylmalonyl-CoA as an extending unit, and a TE. In some embodiments of the invention, the loading module capable of using isobutyryl-CoA as a starter unit comprises $AT_L$, $ACP_L$ and KS1 of Ave Load-Mod1, and a cMT domain between the $AT_L$ and $ACP_L$ domains. In some embodiments of the invention, the module capable of extending using 2-methylmalonyl-CoA as an extending unit comprises mmAT of Ave Load-Mod1, and DH, ER, KR, ACP of DEBS Mod4 or Nan Mod2. The TE can be any suitable TE, such as an Ery TE. In some embodiments of the invention, the PKS comprises the structure depicted in FIG. 3.

Nucleic Acids Encoding the PKS

The present invention provides for a recombinant nucleic acid that encodes a polyketide synthase (PKS) of the present invention. The recombinant nucleic acid can be a double-stranded or single-stranded DNA, or RNA. The recombinant nucleic acid can encode an open reading frame (ORF) of the PKS of the present invention. The recombinant nucleic acid can also comprise promoter sequences for transcribing the ORF in a suitable host cell. The recombinant nucleic acid can also comprise sequences sufficient for having the recombinant nucleic acid stably replicate in a host cell. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present invention. The present invention provides for a host cell comprising any of the recombinant nucleic acid and/or PKS of the present invention. In some embodiments, the host cell, when cultured under a suitable condition, is capable of producing the trimethylpentanoic acid.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

The vectors may be chosen to contain control sequences operably linked to the resulting coding sequences in a manner that expression of the coding sequences may be effected in an appropriate host. Suitable control sequences include those that function in eukaryotic and prokaryotic host cells. If the cloning vectors employed to obtain PKS genes encoding derived PKS lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for single cell cultures of various types of organisms are well known in the art. Control systems for expression in suitable host cells, such as yeast and prokaryotic host cells, are widely available and are routinely used. Control elements include promoters, optionally containing operator sequences, and other elements depending on the nature of the host, such as ribosome binding sites. Particularly useful promoters for prokaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla), bacteriophage lambda PL, and T5. In addition, synthetic promoters, such as the tac promoter (U.S. Pat. No. 4,551,433; hereby incorporated by reference), can be used.

As noted, particularly useful control sequences are those which themselves, or with suitable regulatory systems, activate expression during transition from growth to stationary phase in the vegetative mycelium. Illustrative control sequences, vectors, and host cells of these types include the modified *Streptomyces coelicolor* CH999 and vectors described in PCT publication no. WO 96/40968 and similar strains of *Streptomyces lividans*. See U.S. Pat. Nos. 5,672,491; 5,830,750; 5,843,718; and 6,177,262, each of which is hereby incorporated by reference. Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of CaCl$_2$ or other agents, such as divalent cations, lipofection, DMSO, protoplast transformation, conjugation, and electroporation.

Host Cells Comprising the PKS

The present invention provides for a host cell comprising any of the recombinant nucleic acid and/or PKS of the present invention. In some embodiments, the host cell, when cultured, is capable of producing the trimethylpentanoic acid. The host cell can be a eukaryotic or a prokaryotic cell. Suitable eukaryotic cells include yeast cells, such as from the genus *Saccharomyces* or *Schizosaccharomyces*. A suitable species from the genus *Saccharomyces* is *Saccharomyces cerevisiae*. A suitable species from the genus *Schizosaccharomyces* is *Schizosaccharomyces pombe*. Suitable prokaryotic cells include *Escherichia coli* or *Streptomyces* species.

Production of polyketides in a host cell, such as *E. coli*, employing natural or synthetic PKSs has been achieved previously (Menzella, H. G., S. J. Reisinger, M. Welch, J. T. Kealey, J. Kennedy, R. Reid, C. Q. Tran, and D. V. Santi. 2006. Redesign, synthesis and functional expression of the 6-deoxyerythronolide B polyketide synthase gene cluster. *J Ind Microbiol Biotechnol* 33:22-8; Pfeifer, B. A., S. J. Admiraal, H. Gramajo, D. E. Cane, and C. Khosla. 2001. Biosynthesis of complex polyketides in a metabolically engineered strain of *E. coli*. *Science* 291:1790-2; incorporated by reference herein). One skilled in the art can use *E. coli* 207-3 (Lau, J., C. Tran, P. Licari, and J. Galazzo. 2004. Development of a high cell-density fed-batch bioprocess for the heterologous production of 6-deoxyerythronolide B in *E. coli*. *J Biotechnol* 110:95-103; incorporated by reference herein) or an engineered derivative for production of compound 1 or 2. This strain contains the genes sfp, encoding the activity required for phophopantetheinylation of the ACP domains of PKS-A and PKS-B, as well as prpE, encoding propionyl-CoA synthetase, that converts propionate to propionyl-CoA, accA-pccB, which encodes the enzyme complex that converts propionyl-CoA to 2S-methylmalonyl-CoA, the extender substrate used for PKS-A and PKS-B.

The PKS can be in a host cell, or isolated or purified. The PKS can synthesize the trimethylpentanoic acid in vivo (in a host cell) or in vitro (in a cell extract or where all necessary chemical components or starting materials are provided). The present invention provides methods of producing the trimethylpentanoic acid using any of these in vivo or in vitro means.

In some embodiments of the invention, when the host cell comprises the PKS comprising a loading module which loads a pivaloyl-CoA, when the host cell can further comprise one or more nucleic acids encoding and capable of expressing biosynthetic enzymes for synthesizing pivaloyl-CoA, or when the host cell is cultured pivaloyl-CoA can be exogenously fed to the host cell by having pivalate being present in the culture medium. All hosts contain short chain acyl-CoA synthetases that catalyze the conversion of pivalate into pivaloyl-CoA.

In some embodiments of the invention, when the host cell comprises the PKS comprising a loading module which loads a pivaloyl-CoA, when the host cell can further comprise one or more nucleic acids encoding and capable of expressing biosynthetic enzymes for synthesizing isobutyryl-CoA and a SAM-dependent isobutyryl-CoA methyltransferase. The host cell can either further comprise one or more nucleic acids encoding and capable of expressing biosynthetic enzymes, or functional variants thereof, for synthesizing isobutyryl-CoA, or when the host cell is cultured isobutyryl-CoA can be exogenously fed to the host cell by having isobutyrate being present in the culture medium. The SAM-dependent isobutyryl-CoA methyltransferase catalyzes the following reaction:

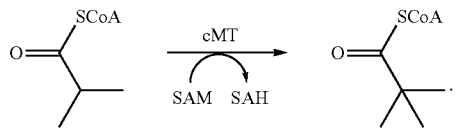

In some embodiments of the invention, when the host cell comprises the PKS comprising a loading module which loads an isobutyryl-CoA, when the host cell can further comprise one or more nucleic acids encoding and capable of expressing biosynthetic enzymes for synthesizing isobutyryl-CoA, or when the host cell is cultured isobutyryl-CoA can be exogenously fed to the host cell by having isobutyrate being present in the culture medium. See FIG. 5.

Isobutyryl-CoA can be synthesized from valine using the following enzymes: IlvE, PdhD, BfmBB, BfmBAA, and BfmBAB, or functional variants thereof.

Isobutyryl-CoA can be synthesized from 2-oxovalerate using the following enzymes: PdhD, BfmBB, BfmBAA, and BfmBAB or functional variants thereof.

An example of a suitable IlvE is *E. coli* IlvE. The amino acid sequence of *E. coli* IlvE (GenBank accession no. AAA24022) comprises:

```
  1 mttkkadyiw fngemvrwed akvhvmshal hygtsvfegi rcydshkgpv vfrhrehmqr 61 lhdsakiyrf pvsqsidelm eacrdvirkn nitsayirpl ifvgdvgmgv nppagystdv 121 iiaafpwgay lgaealeqgi damvsswnra apntiptaak aggnylssll vgsearrhgy 181 qegialdvng yisegagenl fevkdgvlft ppftssalpg itrdaiikla kelgievreq 241 vlsreslyla devfmsgtaa eitpvrsvdg iqvgegrcgp vtkriqqaff glftgetedk 301 wgwldqvnq (SEQ ID NO: 1)
```

An example of a suitable PdhD is *Bacillus subtilis* PdhD. The amino acid sequence of *B. subtilis* PdhD (GenBank accession no. AAC24935) comprises:

(SEQ ID NO: 2)

```
  1 mvvgdfpiet dtlvigagpg gyvaairaaq lgqkvtvvek atlggvclnv gcipskalin
 61 aghryenakh sddmgitaen vtvdftkvqe wkasvvnklt ggvagllkgn kvdvvkgeay
121 fvdsnsvrvm densaqtytf knaiiatgsr pielpnfkys ervlnstgal alkeipkklv
181 vigggyigte lgtayanfgt elvileggde ilpgfekqms slvtrrlkkk gnveihtnam
241 akgveerpdg vtvtfevkge ektvdadyvl itvgrrpntd elgleqvgie mtdrgivktd
301 kqcrtnvpni yaigdiiegp plahkasyeg kiaaeaiage paeidylgip avvfsepela
361 svgyteaqak eegldivaak fpfaangral slnetdgfmk litrkedglv igaqiagasa
421 miselsla ieggmtaedi amtihahptl geitmeaaev aigspihivk
```

An example of a suitable BfmBB is *Bacillus subtilis* BfmBB. The amino acid sequence of *B. subtilis* BfmBB (GenBank accession no. BAA12600) comprises:

```
  1 maieqmtmpq lgesvtegti skwlvapgdk vnkydpiaev mtdkvnaevp ssftgtitel
 61 vgeegqtlqv gemickiete ganpaeqkqe qpaaseaaen pvaksagaad qpnkkryspa
121 vlrlagehgi dldqvtgtga ggritrkdiq rlietggvqe qnpeelktaa papksaskpe
181 pkeetsypas aagdkeipvt gvrkaiasnm krskteipha wtmmevdvtn mvayrnsikd
241 sfkktegfnl tffaffvkav aqalkefpqm nsmwagdkii qkkdinisia vatedslfvp
301 viknadekti kgiakditgl akkvrdgklt addmqggtft vnntgsfgsv qsmgiinypq
361 aailqvesiv krpvvmdngm iavrdmvnlc lsldhrvldg lvcgrflgry kqilesidek
421 tsvy (SEQ ID NO: 3)
```

An example of a suitable BfmBAA is *Bacillus subtilis* BfmBAA. The amino acid sequence of *B. subtilis* BfmBAA (GenBank accession no. BAA12598) comprises:

```
  1 mstnrhgalg ltdqeavdmy rtmllarkid ermwllnrsg kipfviscqg qeaaqvgaaf
 61 aldremdyvl pyyrdmgvvl afgmtakdlm msgfakaadp nsggrqmpgh fgqkknrivt
121 gsspvttqvp havgialagr mekkdiaafv tfgegssnqg dfheganfaa vhklpvifmc
181 ennkyaisvp ydkqvaceni sdraigygmp gvtvngndpl evyqavkear erarrgegpt
241 lietisyrlt phssddddss yrgreeveea kksdplltyq aylketglls deieqtmlde
301 imaivneatd eaenapyaap esaldyvyak (SEQ ID NO: 4)
```

An example of a suitable BfmBAB is *Bacillus subtilis* BfmBAB. The amino acid sequence of *B. subtilis* BfmBAB (GenBank accession no. BAA12599) comprises:

```
  1 msvmsyidai nlamkeemer dsrvfvlged vgrkggvfka taglyeqfge ervmdtplae
 61 saiagvgiga amygmrpiae mgfadfimpa vnqiiseaak iryrsnndws cpivvrapyg
121 ggvhgalyhs qsveaifanq pglkivmpst pydakgllka avrdedpvlf fehkrayrli
181 kgevpaddyv lpigkadvkr egdditvity glcvhfalqa aerlekdgis ahvvdlrtvy
241 pldkeaiiea asktgkvllv tedtkegsim sevaaiiseh clfdldapik rlagpdipam
301 aptmekyf mvnpdkveaa mrelaef (SEQ ID NO: 5)
```

In some embodiments of the invention, when the host cell comprises the PKS comprising an extending module which loads a methylmalonyl-CoA, when the host cell can further comprise one or more nucleic acids encoding and capable of expressing biosynthetic enzymes, or functional variants thereof, for synthesizing methylmalonyl-CoA from propionate, and the host cell is either capable of synthesizing propionate or propionate is exogenously fed to the host cell by having propionate being present in the culture medium.

Propionyl-CoA synthetase converts propionate to propionyl-CoA. An example of a suitable propionyl-CoA synthetase is *Salmonella typhimurium* PrpE. The amino acid sequence of S. *typhimurium* PrpE (GenBank accession no. AAC44817) comprises:

```
  1 msfsefyqrs inepeafwae qarridwrqp ftqtldhsrp pfarwfcggt tnlchnavdr
 61 wrdkqpeala liayssetde ertftfsqlh devnivaaml lslgvqrgdr vlvympmiae
121 aqitllacar igaihsvvfg gfashsvaar iddarpaliv sadagarggk ilpykklldd
181 aiaqaqhqpk hvllvdrgla kmawvdgrdl dfatlrqqhl gasvpvawle snetscilyt
241 sgttgkpkgv qrdvggyava latsmdtifg gkaggvffca sdigwvvghs yivyapllag
301 mativyeglp typdcgvwwk ivekyqvnrm fsaptairvl kkfptaqirn hdlsslealy
361 lagepldept aswvtetlgv pvidnywqte sgwpimalar alddrpsrlg spgvpmygyn
421 vqllnevtge pcginekgml viegplppgc iqtiwgddar fvktywslfn rqvyatfdwg
481 irdaegyyfi lgrtddvini aghrlgtrei eesissypnv aevavvgikd alkgqvavaf
541 vipkqsdtla dreaardeen aimalvdnqi ghfgrpahvw fvsqlpktrs gkmlrrtiqa
601 icegrdpgdl ttiddpaslq qirqaiee (SEQ ID NO: 6)
```

Propionyl-CoA carboxylase converts propionyl-CoA to 2-[S]-methylmalonyl-CoA. An example of a suitable propionyl-CoA carboxylase is *Streptomyces coelicolor* PccA/AccB. The amino acid sequence of *S. coelicolor* PccA (GenBank accession no. NP_627007) comprises:

```
                                                       (SEQ ID NO: 7)
  1 mfdtvlvanr geiavrvirt lrsmgvrsva vfsdadadar hvreaddavr igpapatesy
 61 lsverllaaa artgaqavhp gygflaenag faraceeagl vfigpsadai almgdkirak
121 etvraagvpv vpgssgsglt deqladaare igtpvllkps aggggkgmrl vrdtavlade
181 iaaarreara sfgddtllve rwidrprhie iqvladghgg vvhlgerecs lqrrhqkvie
241 eapsvlldea traamgeaav qaarscgyrg agtvefivpg sdpsqyyfme mntrlqvehp
301 vtelvtgldl vewqlrvaag eplgfgqedv rltghaiear lcaedpargf lpsggtvlrl
361 repegdgvrt dsglsegtev gslydpmlsk viaygpdret alrrlraala gtvtlgvqtn
421 agflrrllah pavvageldt glverevdgl vatdvpeevy eaaaavrlea lrprgdgwtd
481 pfsvpsgwrm ggepkaaafh lrvtdpveht prgthtvtgd rvtvtldgvr htfhraadwl
541 grdgdawqvr dhdpvaasln rsahagadsl tapmpgtvtv vkvavgdevs agqsllvvea
601 mkmehvisap hagtvaeldv apgttvamdq vlaviaptdd ateeta
```

The amino acid sequence of *S. coelicolor* AccB (GenBank accession no. 1XNV_A) comprises:

```
                                                       (SEQ ID NO: 8)
  1 msepeeqqpd ihttagklad lrrrieeath agsaravekq hakgkltare ridllidegs
 61 fveldefarh rstnfgldan rpygdgvvtg ygtvdgrpva vfsqdftvfg galgevygqk
121 ivkvmdfalk tgcpvvgind sggariqegv aslgaygeif rrnthasgvi pqislvvgpc
181 aggavyspai tdftvmvdqt shmfitgpdv iktvtgedvg feelggarth nstsgvahhm
241 agdekdavey vkqllsylps nnlseppafp eeadlavtde daeldtivpd sanqpydmhs
301 viehvlddae ffetqplfap niltgfgrve grpvgivanq pmqfagcldi tasekaarfv
361 rtcdafnvpv ltfvdvpgfl pgvdqehdgi irrgaklifa yaeatvplit vitrkafgga
421 ydvmgskhlg adlnlawpta qiavmgagga vnilhrrtia dagddaeatr arliqeyeda
481 llnpytaaer gyvdavimps dtrrhivrgl rqlrtkresl ppkkhgnipl
```

In another embodiment, the host cell, such as *E. coli*, does not naturally produce methylmalonyl-CoA, but can produce methylmalonyl-CoA from malonyl-CoA, a common intermediate in all hosts, in accordance with the methods and recombinant DNA vectors provided by the invention. Generally, these methods and vectors enable a host cell that does not produce methylmalonyl-CoA to produce it by providing that cell with one or more or all of the following enzymatic activities: malonyl-CoA reductase (MCR), malonate semialdehyde reductase (MSR), 3-hydroxypropionyl-CoA synthase (HPCS), 3-hydroxypropionyl-CoA dehydratase (HPCD), acryloyl-CoA reductase (ACR), and propionyl-CoA carboxylase. These enzymatic activities can be provided by enzymes described herein, or functional variants thereof.

Figure 5:
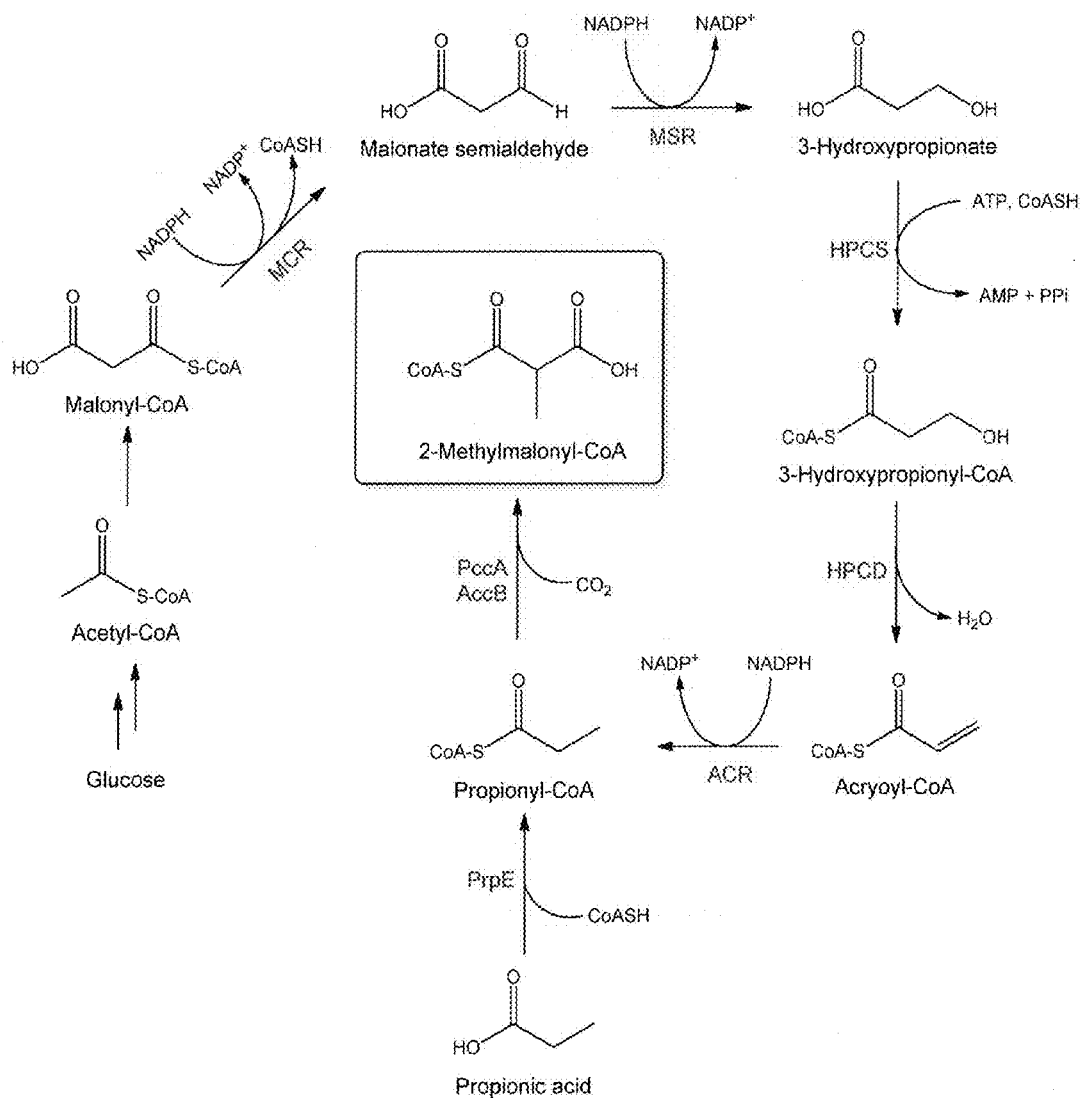
FIG. 5 shows a pathway for synthesizing 2-methylmalonyl-CoA provided by the invention.

An example of suitable Pcc genes are PccA and AccB from *Streptomyces coelicolor*, as shown in FIG. 5. An example of an MCR is the *Sulfolobus tokodaii* MCR. The amino acid sequence of *S. tokodaii* MCR (GenBank Accession No. NP_378167) comprises:

```
                                                    (SEQ ID NO: 9)
  1 milmrrtlka ailgatglvg ieyvrmlsnh pyikpaylag kgsvgkpyge vvrwqtvgqv 61 pkeiadmeik ptdpklmddv diifsplpqg aagpveeqfa kegfpvisns pdhrfdpdvp 121 llvpelnpht islideqrkr rewkgfivtt plctaqgaai plgaifkdyk mdgafittiq 181 slsgagypgi psldvvdnil plgdgydakt ikeifrilse vkrnvdepkl edvslaatth 241 riatihghye vlyvsfkeet aaekvketle nfrgepqdlk lptapskpii vmnedtrpqv 301 yfdrwagdip gmsvvvgrlk qvnkrmirlv slihntvrga agggilaael lvekgyiek.
```

An example of an MSR is the *Metallosphaera sedula* MSR. The amino acid sequence of *M. sedula* MSR (GenBank Accession No. YP_001192057) comprises:

```
  1 mtekvsvvga gvigvgwatl faskgysysl ytekketldk gieklrnyvq vmknnsqite 61 dvntvisrvs pttnldeavr ganfvieavi edydakkkif gyldsvldke vilasstsgl 121 litevqkams khperaviah pwnpphllpl veivpgekts mevvertksl mekldrivvv 181 lkkeipgfig nrlafalfre avylvdegva tvedidkvmt aaiglrwafm gpfltyhlgg 241 geggleyffn rgfgyganew mhtlakydkf pytgvtkaiq qmkeysfikg ktfqeiskwr 301 dekllkvykl vwek. (SEQ ID NO: 10)
```

An example of an HPCS is the *Sulfolobus tokodaii* HPCS. The amino acid sequence of *S. tokodaii* HPCS (GenBank Accession No. NP_376686) comprises:

```
                                                    (SEQ ID NO: 11)
  1 mteklseqlq qlgeqnleek adynmryyky lykksieepd kfwgelaeel itwyepwkqa 61 fvqeeglltk wfvggklnas ynavdrhlns hrkykaaifw esekgekkvv tyqdlfyevn 121 kwanalrelg vkkgdrvtiy mpltpegvia klavarlgai hsvvfagfga qaladriada 181 gakvvitada yyrrgklvel kktvdealni lgdkspvqkv lvykrtgtei pfkegrdvyf 241 devgkykyie pvpveatepl filytsgttg kpkgivhstg gylvgtavml lwsyglsgen 301 dvlfntsdig wivghsyity splvmgrsiv iyesapdypy pdkwaemiek yrattfgtsa 361 tairtlmkyg edyvkqhdls slriivtnge plnyapwkwg levvgggkvf mshqwwqtet 421 ggpnigyipg vvylpmksgp avgfalpgnk vtvvneegke tkprergylv mlppfppmmm 481 igmwndpdne rlkktyfskf pgiyypgdya midedgyiwv mgradetikv aahrigagev 541 esivtshpav aeaaavgipd pvkgeavhlf vvlkvgykps pqlareigeh vrkymgaivt 601 pevhfvdklp ktrsgkimrr vikavmmgqs agdittlede asmdeikkav eefkkslsq.
```

An example of an HPCD is the *Metallosphaera sedula* HPCD. The amino acid sequence of *M. sedula* HPCD (GenBank Accession No. YP001192065) comprises:

```
  1 mefetietkk egnlfwitln rpdklnalna klleeldrav sqaesdpeir viiitgkgka 61 fcagaditqf nqltpaeawk fskkgreimd kiealskpti amingyalgg glelalacdi 121 riaaeeaqlg lpeinlgiyp gyggtqrltr vigkgralem mmtgdripgk daekyglvnr 181 vvplanleqe trklaekiak kspislalik evvnrgldsp llsglalesv gwgvvfsted 241 kkegvsafle kreptfkgk. (SEQ ID NO: 12)
```

An example of an ACR is the *Sulfolobus tokodaii* ACR. The amino acid sequence of *S. tokodaii* ACR (GenBank Accession No. Q975C8) comprises:

```
  1 mkaivvpgpk qgykleevpd pkpgkdevii rvdraalcyr dllqlqgyyp rmkypvilgh 61 evvgtieevg enikgfevgd kvisllyapd gtceycqige eaychhrlgy seeldgffae 121 kakikvtslv kvpkgtpdeg avlvpcvtgm iyrgirragg irkgelvlvt gasggvgiha 181 iqvakalgak vigvttseek akiikqyady vivgtkfsee akkigdvtlv idtvgtptfd 241 eslkslwmgg rivqignvdp sqiynlrlgy iilkdlkivg hasatkkdae dtlkltqegk 301 ikpviagtvs lenidegykm ikdknkvgkv lvkp. (SEQ ID NO: 13)
```

Methods of Using the PKS

The present invention provides a method of producing a trimethylpentanoic acid, comprising: providing a host cell of the present invention, and culturing said host cell in a suitable culture medium such that the trimethylpentanoic acid is produced. The method can further comprise isolating said trimethylpentanoic acid from the host cell and the culture medium. The method can further comprise reducing the isolated trimethylpentanoic acid to produce a trimethylpenatnol or iso-octane. A variety of methods for heterologous expression of PKS genes and host cells suitable for expression of these genes and production of polyketides are described, for example, in U.S. Pat. Nos. 5,843,718; 5,830,750 and 6,262,340; WO 01/31035, WO 01/27306, and WO 02/068613; and U.S. Patent Application Pub. Nos. 20020192767 and 20020045220; hereby incorporated by reference.

The present invention provides for a composition comprising a trimethylpentanoic acid isolated from a host cell from which the trimethylpentanoic acid is produced, and trace residues and/or contaminants of the host cell. Such trace residues and/or contaminants include cellular material produced by the lysis of the host cell.

The iso-octane produced by reducing the trimethylpentanoic acid is useful as a fuel as a chemical source of energy that can be used as an alternative to petroleum derived fuels, ethanol and the like.

The present invention has one or more of the following advantages: (1) it reduces the dependence on oil for producing certain chemicals, and (2) it serves as a means of capture and sequestration of carbon from the atmosphere.

The present invention describes the uses of PKSs to produce 2,2,4-trimethylpentanoic acid and 2,4,4-trimethylpentanoic acid. These compounds are converted to 2,2,4-trimethylpentane, also called iso-octane, by well established chemical methods. The acid is converted to the corresponding alcohol by treatment with the agent lithium aluminum hydride (LiAlH4). Two routes can be used to convert the alcohol to the alkane. In the first, the alcohol is treated with p-toluenesulfonyl chloride (tosyl chloride) to form the tosylate, which is then reacted with LiALH4 again to convert it to the alkane. The alcohol, 2,4,4-trimethyl-1-pentanol can be reduced to the 1-olefin by treatment with sulfuric acid. The olefin is converted to the alkane by reduction with hydrogen gas in the presence of a platinum catalyst.

The invention having been described, the following examples are offered to illustrate the subject invention by way of illustration, not by way of limitation.

Example 1

Production of Iso-Octane from 2,2,4-Trimethylpentanoic Acid Through Methylation of 2,4-Dimethyl Pentanoic Acid PKS-A (FIG. 2) is designed to produce 2,2,4-trimethylpentanoic acid through the condensation of isobutyryl-CoA and 2-methylmalonyl-CoA, both of which can be produced intracellularly in the microbial host, followed by full reduction of the β-carbonyl formed from the condensation to the corresponding methylene center, followed by the methylation of the α-carbon. PKS-A is composed of a loading module and a single extender module. The loading module is from the avermectin (ave) PKS (from *Streptomyces avermitilis*) which accepts isobutyryl-CoA (Marsden, A. F., B. Wilkinson, J. Cortes, N.J. Dunster, J. Staunton, and P. F. Leadlay. 1998. Engineering broader specificity into an antibiotic-producing polyketide synthase. Science 279:199-202; incorporated by reference herein). The loading module from the lipomycin PKS also accepts isobutyryl-CoA (Bihlmaier C., E. Welle, C. Hofmann, K. Welzel, A. Vente, E. Breitling, M. Müller, S. Glaser, and A. Bechthold. 2006. Biosynthetic gene cluster for the polyenoyltetramic acid alpha-lipomycin. Antimicrob Agents Chemother. 50:2113-21; incorporated by reference herein) and can be used in place of the ave loading module. Module 1 comprises 5 domains: the KS and ACP for the condensation, the mmAT domain that is specific for 2-methylmalonyl-CoA, the DH, ER and KR domains to reduce the β-carbonyl group produced from the condensation to the methylene center, and the cMT domain to methylate the α-carbon, creating a geminal dimethyl at C2. The TE domain is present to release the nascent polyketide chain. In PKS-A, the mmAT-DH-ER-KR- and ACP domains are the mmAT- DH-ER-KR- and ACP domains of module 4 of the erythromycin PKS or of module 2 of the Nan PKS. The TE domain is the TE domain of the erythromycin PKS. The cMT domain in PKS-A is the cMT domain in module 8 of the epothilone PKS. A cMT domain from another PKS such as the cMT domains from module 4 or 9 of the bryostatin PKS, or module 2 of the disorazole PKS can be used in place of cMT domain from module 8 of the epothilone PKS in the construction of PKS-A. In the construction of PKS-A the cMT domain is introduced between the DH and ER domain, specifically between the segments corresponding to DH2 and pseudo-KR (Meir, T. et al. 2008. Science 321:1315). PKS-A is designed to be produced as a single polypeptide in E. coli.

Isobutyryl-CoA.

Figure 4:
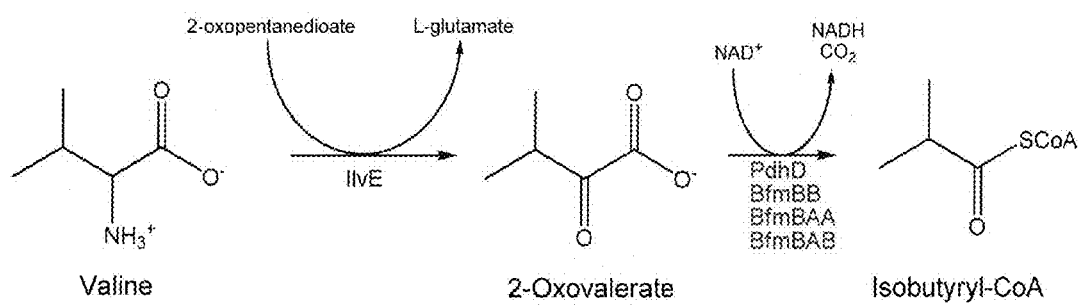
FIG. 4 shows a pathway for synthesizing isobutyryl-CoA provided by the invention.

The starter substrate isobutyryl-CoA for PKS-A is produced from the metabolism of valine. To overproduce isobutyryl-CoA, as shown in FIG. 4, the E. coli gene ilvE, encoding the enzyme branched-chain amino acid transaminase (Massey, L. K., J. R. Sokatch, and R. S. Conrad. 1976. Branched-chain amino acid catabolism in bacteria. Bacteriol Rev 40:42-54; incorporated by reference herein), and the genes pdhD, bfmBB, bfmBAA, bfmBAB for the enzyme complex of branched-chain α-keto acid dehydrogenase from *Bacillus subtilis* (Caspi, R., H. Foerster, C. A. Fulcher, P. Kaipa, M. Krummenacker, M. Latendresse, S. Paley, S. Y. Rhee, A. G. Shearer, C. Tissier, T. C. Walk, P. Zhang, and P. D. Karp. 2008. The MetaCyc Database of metabolic pathways and enzymes and the BioCyc collection of Pathway/Genome Databases. Nucleic Acids Res 36:D623-31; incorporated by reference herein) are overexpressed.

2-Methylmalonyl-CoA.

The extender substrate 2-methylmalonyl-CoA for PKS-A is produced in E. coli 207-3 in one of two ways. Exogenously fed propionic acid is converted first to propionyl-CoA by the action of PrpE, and then to 2-methylmalonyl-CoA through the *Streptomyces coelicolor* enzymes PccA and AccB, as outlined in FIG. 5. The corresponding genes for the PrpE, PccA and AccB are present and overexpressed in E. coli 207-3. As an alternative, 2-methylmalonyl-CoA is produced from malonyl-CoA through the addition and overexpression of genes corresponding to MCR, MSR, HPCS, HPCD, ACR, PccA, and AccB, as outlined in FIG. 5.

Example 2

Figure 3:
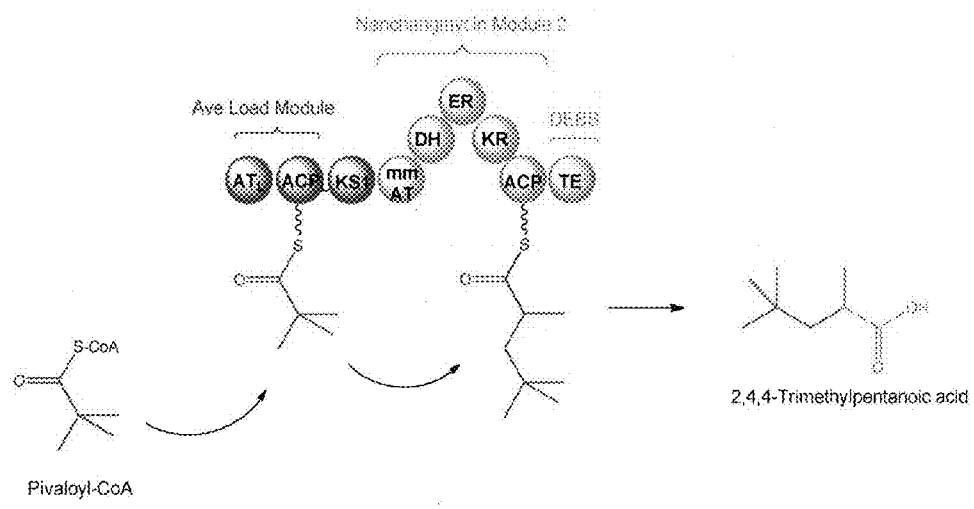
FIG. 3 shows two examples of PKS-B constructs, each designed to produce 2,4,4-trimethylpentanoic acid provided by the invention.
Figure 3:
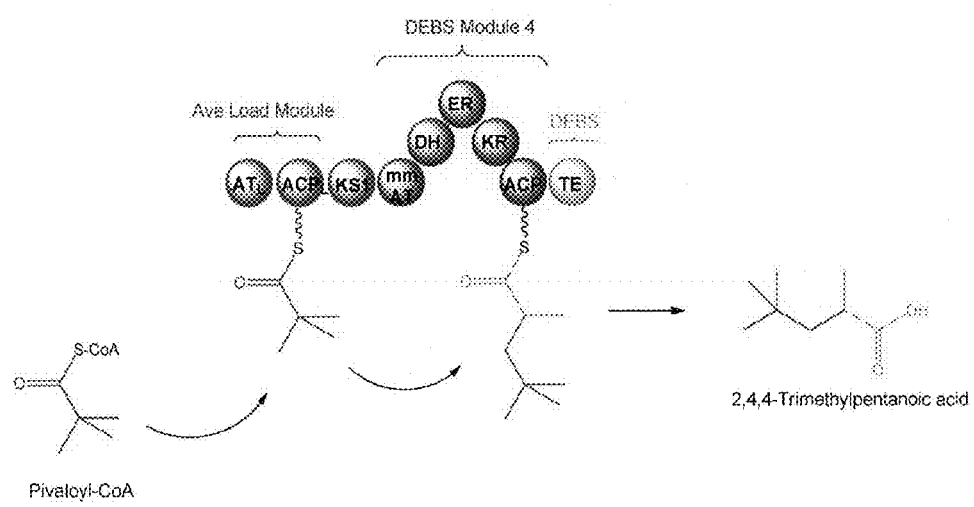

Production of Iso-Octane from 2,4,4-Trimethylpentanoate Produced by Condensation of Pivaloyl-CoA and Methylmalonyl-CoA PKS-B (FIG. 3) is designed to produce compound 2 through the condensation of pivaloyl-CoA and methylmalonyl-CoA followed by full reduction of the β-carbonyl formed to the corresponding methylene center. PKS-B comprises a loading module and a single extender module and is similar to PKS-A with the exception that it does not contain the C-methylation domain present in the latter. The simplified design of PKS-B enables the construction from two contiguous, naturally-occurring segments: $AT_L$-KS domains from the avermectin PKS and mmAT-ACP of module 4 of DEBS, or module 2 of the Nan PKS. The TE domain of the erythromycin PKS is added as the third component. As in the case of PKS-A, the construct is expressed as a single gene in E. coli. An abbreviated scheme for the biosynthesis of compound 2 catalyzed by PKS-B is illustrated in FIG. 3. The scheme shows the starter as 2,2-dimethylpropionyl-CoA (pivaloyl-CoA) which condenses with 2-methymalonyl-CoA. Following reduction, the diketide 2,4,4-trimethylpentanoyl-ACP is produced The TE domain releases 2,4,4-trimethylpentanoate (2).

2-Methylmalonyl-CoA.

The extender substrate 2-methylmalonyl-CoA for PKS-B is produced in E. coli 207-3 in as described in Example 1.

Pivaloyl-CoA.

The $AT_L$-domain of the ave PKS can use pivaloyl-CoA as a starter for polyketide synthesis (Rezanka, T., L. Siristova, O, Schreiberova, M. Rezanka. 2011. Pivalic acid acts as a starter unit in a fatty acid and antibiotic biosynthetic pathway in *Alicyclobacillus, Rododcoccus* and *Streptomyces*. 2011. Environmental Microbiol. 13:1577-1589; incorporated by reference herein). Exogenously fed pivalate is converted to pivaloyl-CoA by the host's native acyl-CoA synthetases.

Example 3

Conversion of 2,2,4-Trimethylpentanoic Acid and 2,4,4-Trimethylpentanoic to Iso-Octane Both 2,2,4-trimethylpentanoic acid and 2,4,4-trimethylpentanoic acid is reduced to the corresponding 1-alcohol by treatment with lithium aluminum hydride ($LiAlH_4$). Subsequently, 2,2,4-trimethyl-1-pentanol and 2,4,4-trimethyl-1-pentanol are reduced to the corresponding alkane, 2,2,4-trimethylpentane (iso-ocatane) by treatment with sulfuric acid followed by treatment with hydrogen gas using a platinum catalyst. An alternative method is to first treat the alcohol with p-toluenesulfonyl chloride and then react the resulting tosylate with $LiAlH_4$ to produce isooctane.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What we claim is:

1. A method of producing a trimethylpentanoic acid, comprising: providing a prokaryotic host cell and culturing said host cell in a suitable culture medium such that the trimethylpentanoic acid is produced, wherein the host cell comprises a recombinant nucleic acid encoding a hybrid polyketide synthase (PKS) having a module from two or more PKS polypeptides, and further, wherein the hybrid PKS comprises: a loading module comprising an acyltransferase (AT) and an acyl carrier protein (ACP) that uses pivaloyl-CoA as a starter unit, and a module comprising a ketosynthase (KS), methylmalonyl-CoA acyltransferase (mmAT), dehydratase (DH), enoylreductase (ER), ketoreductase (KR), and ACP that uses 2-methylmalonyl-CoA as an extending unit; and a thioesterase (TE).

2. The method of claim 1, further comprising isolating the trimethylpentanoic acid.

3. The method of claim 2, further comprising reducing the trimethylpentanoic acid to produce a trimethylpentanol or an iso-octane.

4. The method of claim 1, wherein the TE is an Ery TE.

5. The method of claim 1, wherein the module that uses 2-methylmalonyl-CoA as an extending unit comprises KS of Ave Load-Mod1, and an mmAT, DH, ER, KR, and ACP of Ery Mod4 or Nan Mod2.

6. The method of claim 1, wherein the loading module comprises $AT_L$ and $ACP_L$ of Ave Load-Mod1.

7. The method of claim 6, wherein the module that uses 2-methylmalonyl-CoA as an extending unit comprises KS of Ave Load-Mod1, and an mmAT, DH, ER, KR, and ACP of Ery Mod4 or NanMod 2.

8. The method of claim 7, wherein the TE is an Ery TE.

9. The method of claim 1, wherein the loading module comprises $AT_L$, $ACP_L$ and KS1 of But Load Module of *Streptomyces rochei*.

10. The method of claim 9, wherein the module that uses 2-methylmalonyl-CoA as an extending unit comprises an mmAT, DH, ER, KR, ACP of Ery Mod4.

11. The method of claim 10, wherein the TE is an Ery TE.

12. The method of claim 1, wherein the host cell comprises a replicon comprising the recombinant nucleic acid encoding the hybrid polyketide synthase, wherein the replicon is stably maintained in the host cell.

13. The method of claim 12, wherein the replicon is a plasmid or vector.

14. The method of claim 13, wherein the vector is an expression vector.

15. The method of claim 1, wherein the host cell further comprises PrpE, and PccA or AccB.

16. The method of claim 1, wherein the host cell further comprises MCR, MSR, HPCS, HPCD, and ACR.

17. The method of claim 1, wherein the host cell is an *Escherichia coli* host cell.

* * * * *